United States Patent [19]
Bernardon

[11] Patent Number: 6,051,243
[45] Date of Patent: Apr. 18, 2000

[54] POLYAROMATIC AMIDE COMPOUNDS AND PHARMACEUTICAL/COSMETIC COMPOSITIONS COMPRISED THEREOF

[75] Inventor: Jean-Michel Bernardon, Le Rouret, France

[73] Assignee: Centre International de Recherches Dermatologiques, Valbonne, France

[21] Appl. No.: 08/969,762

[22] Filed: Nov. 13, 1997

Related U.S. Application Data

[62] Division of application No. 08/356,680, Dec. 15, 1994, Pat. No. 5,709,867.

[30] Foreign Application Priority Data

Dec. 15, 1993 [FR] France .................... 93 15066

[51] Int. Cl.$^7$ .......... A61K 31/40; A61K 31/44; C07D 207/34; C07D 213/75
[52] U.S. Cl. .......... 424/401; 514/346; 514/352; 514/423; 514/424; 514/426; 546/297; 546/298; 546/309; 548/537
[58] Field of Search .................... 546/297, 298, 546/309; 548/537; 514/346, 352, 423, 424, 426; 424/47, 401

[56] References Cited

U.S. PATENT DOCUMENTS

| | | | |
|---|---|---|---|
| 3,829,467 | 8/1974 | Diamond et al. | 562/405 |
| 3,953,428 | 4/1976 | Murakami et al. | 540/330 |
| 5,426,106 | 6/1995 | Kulagowski et al. | 514/233.2 |
| 5,654,331 | 8/1997 | Bernardon | 514/532 |
| 5,688,817 | 11/1997 | Bernardon et al. | 514/346 |

FOREIGN PATENT DOCUMENTS

| | | |
|---|---|---|
| 0 514 264 | 11/1992 | European Pat. Off. . |
| 92/06948 | 4/1992 | WIPO . |

OTHER PUBLICATIONS

Samvelyan et al., Chemical Abstracts, vol. 118, abstract 204725, 1993.
Yoshida et al., Chemical Abstracts, vol. 110, abstract 213341, 1989.
Koike et al., Chemical Abstracts, vol. 110, abstract 187806, 1989.
Guendel, Chemical Abstracts, vol. 103, abstract 105269, 1985.
Engel et al., Chemical Abstracts, vol. 87, abstract 38231, 1977.
Blum et al., Chemical Abstracts, vol. 86, abstract 116260, 1977.
Sato et al., Chemical Abstracts, vol. 71, abstract 13360, 1969.

*Primary Examiner*—Richard L. Raymond
*Attorney, Agent, or Firm*—Burns, Doane, Swecker & Mathis, L.L.P.

[57] ABSTRACT

Novel pharmaceutically/cosmetically-active polyaromatic amides have the structural formula (I):

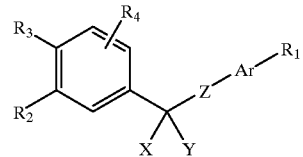

wherein Z is a radical —CO—NH— or —NH—CO—, and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

51 Claims, 2 Drawing Sheets

POLYAROMATIC AMIDE COMPOUNDS AND PHARMACEUTICAL/COSMETIC COMPOSITIONS COMPRISED THEREOF

This application is a divisional of application Ser. No. 08/356,680, filed Dec. 15, 1994, now U.S. Pat. No. 5,709,867.

CROSS-REFERENCE TO COMPANION APPLICATIONS

Copending applications Ser. No. 08/356,913 and Ser. No. 09/357,024, both filed concurrently herewith and assigned to the assignee hereof.

BACKGROUND OF THE INVENTION

Field of the Invention

The present invention relates to novel polyaromatic amide compounds and to pharmaceutical/cosmetic compositions comprised thereof; the subject compounds are especially useful in human or veterinary medicine, or alternatively in cosmetic compositions.

SUMMARY OF TEE INVENTION

The compounds according to the invention display marked activity in the fields of cell differentiation and proliferation, and are particularly useful in the topical and systemic treatment of dermatological conditions associated with a keratinization disorder, dermatological conditions (and the like) including an inflammatory and/or immunoallergic component, and dermal or epidermal proliferations, whether benign or malignant. The subject compounds can, in addition, be used for the treatment of degeneration diseases of the connective tissue, for combating skin aging, whether photoinduced or chronologic, and for treating cicatrization disorders. They are also useful for ophthalmological applications, especially for the treatment of corneopathies.

The compounds according to this invention can also be formulated into cosmetic compositions for body and hair care.

Briefly, the polyaromatic amides according to this invention have the following structural formula (I):

(I)

in which Z is a radical —CO—NH— or —NH—CO—; Ar is a radical selected from among those of the following formulae (a)–(e):

(a)

(b)

(c)

(d)

(e)

wherein % and $R_6$ are as defined below; $R_1$ is (i) a hydrogen atom, (ii) a radical —$CH_3$, (iii) a radical —$CH_2$—O—$R_6$, (iv) a radical —O—$R_6$, (v) a radical —CO—$R_7$, or (vi) a radical —S(O)$_t R_9$ wherein $R_6$, $R_7$, $R_9$ and t are as defined below; X is a hydrogen atom or a lower alkyl radical; Y is (i) a radical of the formula:

(ii) a radical —$CH_2OR_{12}$, (iii) a radical —$COR_{13}$, or (iv) a radical —$(CH_2)_n$—$COR_{14}$ wherein $R_{10}R_{11}$, $R_{12}$, $R_{13}$, $R_{14}$ and n are as defined below; $R_2$ and $R_3$, which may be identical or different, are each a hydrogen atom, a linear or branched alkyl radial having from 1 to 20 carbon atoms, a radical —$OR_6$ or a radical —$SR_6$, wherein $R_6$ is as defined below, with the proviso that $R_2$ and $R_3$ may together form, with the carbon atoms from which they depend, a 5-or 6-membered ring optionally substituted by methyl groups and/or optionally interrupted by an oxygen or sulfur atom; $R_4$ is a hydrogen atom, a halogen atom, a lower alkyl radical or a radical —$OR_6$ wherein $R_6$ is as defined below; $R_5$ has the definition of $R_4$, with the proviso that $R_4$ and $R_5$ may be identical or different; $R_6$ is a hydrogen atom, a linear or branched alkyl radical having from 1 to 20 carbon atoms or a radical —CO—$R_9$ wherein $R_9$ is as defined below and further wherein the radicals $R_6$ may be identical or different; $R_7$ is (a) a hydrogen atom, (b) a lower alkyl radical, (c) a radical of the formula:

wherein R' and R" are as defined below, or (d) a radical —$OR_8$ wherein $R_8$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid or peptide residue; the radicals $R_9$, which may be identical or different, are each a lower alkyl radical; $R_{10}$ is a hydrogen atom or a lower alkyl radical; $R_{11}$ is a hydrogen atom, a lower alkyl radical, a radical —CO—$R_9$ or a radical —COOR$_9$; $R_{12}$ is a radical $R_6$ or a radical —CH$_2$—O—CH$_2$—CH$_2$—O—CH$_3$; $R_{13}$ is a hydrogen atom or a lower alkyl radical; $R_{14}$ is a radical —OR$_8$, or a radical of the formula:

wherein R' and R", which may be identical or different, are each a hydrogen atom, a lower alkyl radical, a mono or polyhydroxyalkyl radical, an optionally substituted aryl radical or an amino acid or peptide or sugar residue, with the proviso that R' and R" may together form, with the nitrogen atom from which they depend, a heterocycle; t is an integer equal to 0, 1 or 2; n is an integer equal to 0 or 1; and with the further proviso that the radicals X and Y may together form a double bond-containing single radical of the formula =N—OR$_6$ or =CH—COR$_{14}$.

This invention also features the salts of the compounds of formula (I) in the event that $R_1$ is a carboxylic acid functional group, as well as the optical and geometric isomers thereof. When the compounds according to the invention are in the form of salts, they are preferably salts of an alkali or alkaline earth metal, or, alternatively, of zinc or of an organic amine.

DETAILED DESCRIPTION OF BEST MODE AND PREFERRED EMBODIMENTS OF THE INVENTION

More particularly according to the present invention, by "lower alkyl radical" is intended an alkyl radical having from 1 to 6 carbon atoms, preferably methyl, ethyl, isopropyl, butyl, tert-butyl and hexyl radicals.

By "linear or branched alkyl radical having from 1 to 20 carbon atoms" is preferably intended methyl, ethyl, propyl, 2-ethylhexyl, octyl, dodecyl, hexadecyl and octadecyl radicals.

By "monohydroxyalkyl radical" is intended a radical preferably having 2 or 3 carbon atoms, especially a 2-hydroxyethyl, 2-hydroxypropyl or 3-hydroxypropyl radical.

By "polyhydroxyalkyl radical" is intended a radical preferably having 3 to 6 carbon atoms and 2 to 5 hydroxyl groups, such as 2,3-dihydroxypropyl, 2,3,4-trihydroxybutyl or 2,3,4,5-tetrahydroxypentyl radicals, or a pentaerythritol residue.

By "aryl radical" is preferably intended a phenyl radical optionally substituted by at least one halogen atom, or a hydroxyl or nitro functional group.

By "aralkyl radical" is preferably intended a benzyl or phenethyl radical optionally substituted by at least one halogen atom, or a hydroxyl or nitro functional group.

By "alkenyl radical" is intended a radical preferably having from 1 to 5 carbon atoms and one or more sites of ethylenic unsaturation, such as, more particularly, the allyl radical.

By "sugar residue" is intended a residue derived especially from glucose, galactose or mannose, or alternatively from glucuronic acid.

By "amino acid residue" is especially intended a residue derived from lysine, glycine or aspartic acid, and by "peptide residue" is more particularly intended a dipeptide or tripeptide residue prepared via the combination of amino acids.

Lastly, by "heterocycle" is preferably intended a piperidino, morpholino, pyrrolidino or piperazino radical, optionally substituted at the 4-position by a $C_1$–$C_6$ alkyl radical or a mono- or polyhydroxyalkyl radical as defined above.

When $R_4$ and $R_5$ in formula (I) represent a halogen atom, it is preferably a fluorine, chlorine or bromine atom.

When $R_1$ represents —O—$R_6$, $R_6$ preferably represents a lower alkyl radical.

Among the compounds of formula (I) according to the present invention, particularly representative are the following:

4-[α-Amino-(5,6,7,8-tetrahydro-5,5,8,8-tetramethyl-2-naphthyl)acetamido]benzoic acid;

4-[α-Methoxyimino-(5,6,7,8-tetrahydro-5,5,8,8-tetramethyl-2-naphthyl)acetamido]benzoic acid;

4-[α-Acetamido-(5,6,7,8-tetrahydro-5,5,8,8-tetramethyl-2-naphthyl)acetamido]benzoic acid;

anti-4-[α-Hydroxyimino-(5,6,7,8-tetrahydro-5,5,8,8-tetramethyl-2-naphthyl)acetamido]benzoic acid;

syn-4-[α-Hydroxyimino-(5,6,7,8-tetrahydro-5,5,8,8-tetramethyl-2-naphthyl)acetamido]benzoic acid;

4-[α-Methoxycarbonyl-(5,6,7,8-tetrahydro-5,5,8,8-tetramethyl-2-naphthyl)acetamido]benzoic acid;

4-[α-Carboxy-(5,6,7,8-tetrahydro-5,5,8,8-tetramethyl-2-naphthyl)acetamido]benzoic acid;

4-[α-Carbamoyl-(5,6,7,8-tetrahydro-5,5,8,8-tetramethyl-2-naphthyl)acetamido]benzoic acid;

2-Hydroxy-4-[α-tert-butoxycarboxamido-(5,6,7,8-tetrahydro-5,5,8,8-tetramethyl-2-naphthyl)acetamido]benzoic acid;

2-Hydroxy-4-[α-amino-(5,6,7,8-tetrahydro-5,5,8,8-tetramethyl-2-naphthyl)acetamido]benzoic acid;

4-[α-Methoxycarbonyl-(5,6,7,8-tetrahydro-5,5,8,8-tetramethyl-2-naphthyl)methylcarbamoyl]benzoic acid;

4-[α-Carboxyl-(5,6,7,8-tetrahydro-5,5,8,8-tetramethyl-2-naphthyl)methylcarbamoyl]benzoic acid;

4-[α-Hydroxymethyl-(5,6,7,8-tetrahydro-5,5,8,8-tetramethyl-2-naphthyl)methylcarbamoyl]benzoic acid;

4-[α-Acetoxymethyl-(5,6,7,8-tetrahydro-5,5,8,8-tetramethyl-2-naphthyl)methylcarbamoyl]benzoic acid;

syn-4-[α-Propyloxyimino-(5,6,7,8-tetrahydro-5,5,8,8-tetramethyl-2-naphthyl)acetamido]benzoic acid;

anti-4-[α-Propyloxyimino-(5,6,7,8-tetrahydro-5,5,8,8-tetramethyl-2-naphthyl)acetamido]benzoic acid;

syn-4-[α-Hexyloxyimino-(5,6,7,8-tetrahydro-5,5,8,8-tetramethyl-2-naphthyl)acetamido]benzoic acid;

anti-4-[α-Hexyloxyimino-(5,6,7,8-tetrahydro-5,5,8,8-tetramethyl-2-naphthyl)acetamido]benzoic acid;

syn-4-[α-Heptyloxyimino-(5,6,7,8-tetrahydro-5,5,8,8-tetramethyl-2-naphthyl)acetamido]benzoic acid;

anti-4-[α-Heptyloxyimino-(5,6,7,8-tetrahydro-5,5,8,8-tetramethyl-2-naphthyl)acetamido]benzoic acid;

syn-4-[α-Nonyloxyimino-(5,6,7,8-tetrahydro-5,5,8,8-tetramethyl-2-naphthyl)acetamido]benzoic acid;

anti-4-[α-Nonyloxyimino-(5,6,7,8-tetrahydro-5,5,8,8-tetramethyl-2-naphthyl)acetamido]benzoic acid;

syn-4-[α-Dodecyloxyimino-(5,6,7,8-tetrahydro-5,5,8,8-tetramethyl-2-naphthyl)acetamido]benzoic acid;

Methyl 5-[α-amino-(5,6,7,8-tetrahydro-5,5,8,8-tetramethyl-2-naphthyl)acetamido]-2-thiophenecarboxylate;

Methyl N-methyl-5-[α-amino-(5,6,7,8-tetrahydro-5,5,8,8-tetramethyl-2-naphthyl)acetamido]-2-pyrrolecarboxylate;

Methyl N-methyl-4-[α-amino-(5,6,7,8-tetrahydro-5,5,8,8-tetramethyl-2-naphthyl)acetamido]-2-pyrrolecarboxylate;

Methyl N-propyl-4-[α-amino-(5,6,7,8-tetrahydro-5,5,8,8-tetramethyl-2-naphthyl)acetamido]-2-pyrrolecarboxylate;

4'-[α-Amino-(5,6,7,8-tetrahydro-5,5,8,8-tetramethyl-2-naphthyl)acetamido]acetophenone;

4-[α-Amino-(5,6,7,8-tetrahydro-5,5,8,8-tetramethyl-2-naphthyl)toluene;

4-[α-Amino-(5,6,7,8-tetrahydro-5,5,8,8-tetramethyl-2-naphthyl)phenyl sulfonylmethane;

4-[α-tert-Butoxycarboxamido-(5,6,7,8-tetrahydro-5,5,8,8-tetramethyl-2-naphthyl)acetamido]-phenylcarboxamide;

4'-[α-Amino-(5,6,7,8-tetrahydro-5,5,8,8-tetramethyl-2-naphthyl)benzyl acetate;

syn-2-Hydroxy-4-[α-hydroxyimino-(5,6,7,8-tetrahydro-5,5,8,8-tetramethyl-2-naphthyl)-acetamido]benzoic acid;

4-[2-Ethoxycarbonyl-2-(5,6,7,8-tetrahydro-5,5,8,8-tetramethyl-2-naphthyl)acrylamido]benzoic acid;

Allyl 4-[2-tert-butoxycarbonyl-2-(5,6,7,8-tetrahydro-5,5,8,8-tetramethyl-2-naphthyl)acrylamido]-benzoate.

According to the present invention, the compounds of formula (I) which are more particularly preferred are those in which X represents a hydrogen atom, Y represents the —$NH_7$ radical, and $R_7$ represents a radical —$OR_8$ wherein $R_7$ and $R_8$ are as defined above.

Figure 1:
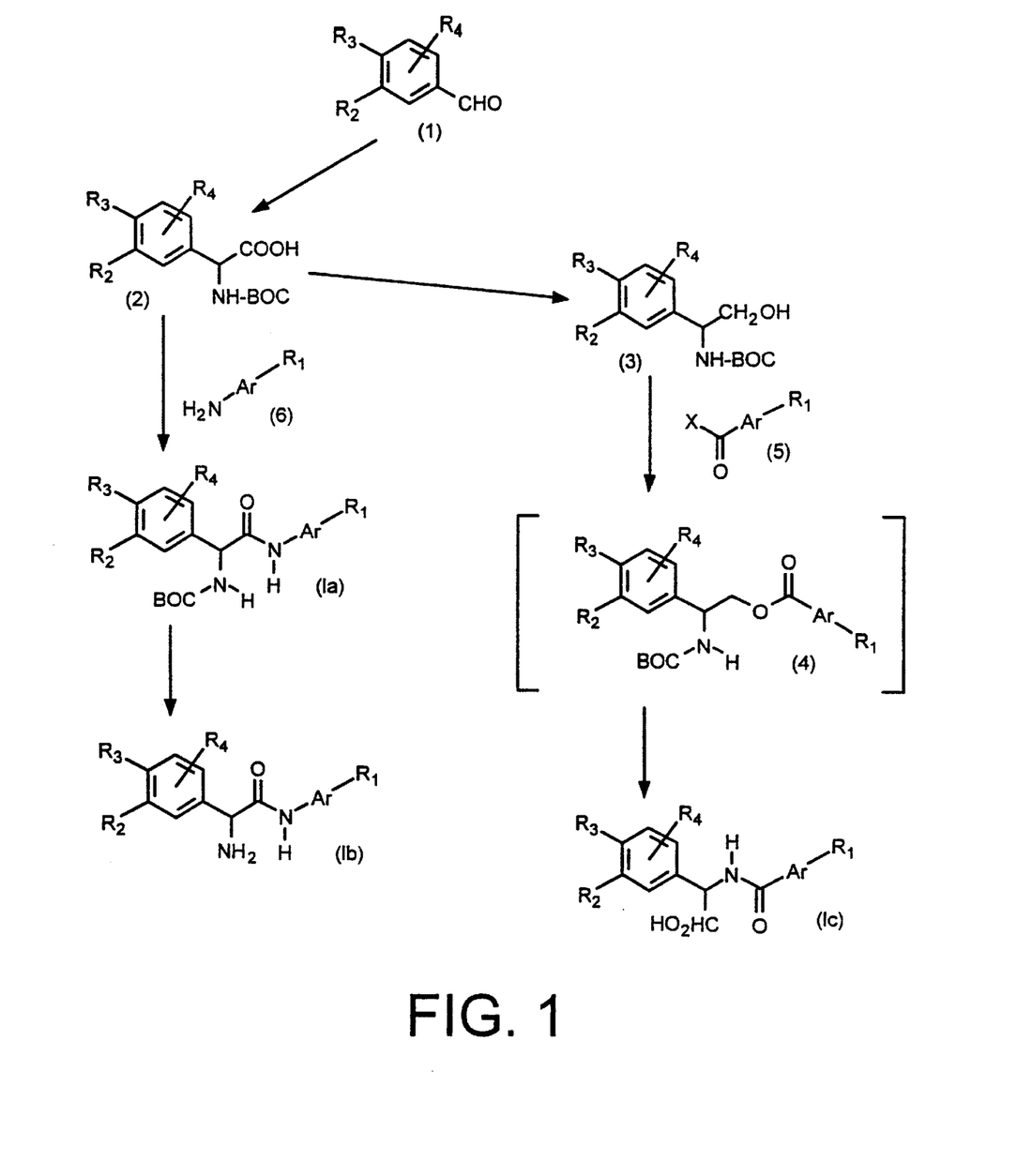
FIGS. 1 and 2 are reaction schemes/mechanisms illustrating syntheses for the preparation of the polyaromatic amides according to the present invention.
Figure 2:
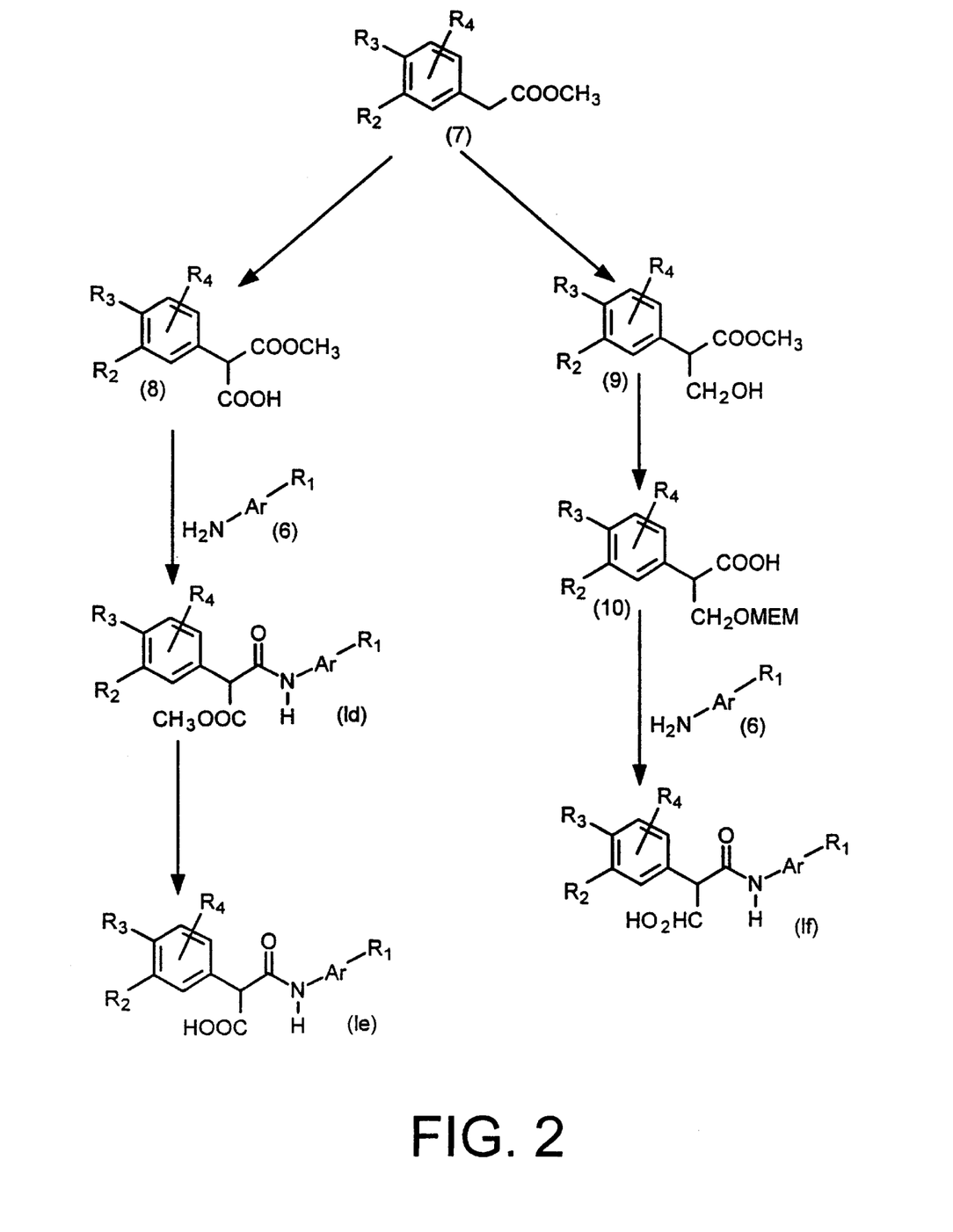

The present invention also features the processes for preparing the compounds of formula (I) via the reaction schemes or mechanisms illustrated in FIGS. 1 and 2.

The derivatives of formula (Ia) can be prepared by a series of reactions comprising the synthesis of a glycine derivative of formula (2) obtained by the Strecker-Buicherer reaction from an aromatic aldehyde of formula (I) and then protecting the amine functional group in the form of carbamate (BOC). The derivative of formula (2) is coupled with the aniline of formula (6) either by means of the acid chloride or in the presence of dicyclohexylcarbodiimide and dimethylaminopyridine in a solvent such as TEF or dichloromethane.

The derivatives of formula (Ib) are prepared from (Ia) by cleaving the carbamate either in the presence of trifluoroacetic acid or in the presence of trimethylsilyl iodide.

The derivatives of formula (Ic) are conveniently prepared from the compound of formula (2) by reduction of the acid functional group via a mixed anhydride with an alkali metal hydride (for example sodium borohydride). The compound (3) thus obtained is coupled with a benzoyl chloride of formula (5) in an organic solvent such as dichloromethane or THF containing a tertiary amine (triethylamine or pyridine).

The compounds of formula (Id) are prepared by a series of reactions comprising lithiation at −78° C. of an acetate of formula (7) with lithium diisopropylamide and then reaction with $CO_2$ in an organic solvent such as THF. The derivative of formula (8) thus obtained is coupled with the aniline of formula (6) either by means of the acid chloride or in the presence of dicyclohexylcarbodiimide and dimethylaminopyridine in a solvent such as THF or dichloromethane.

The compounds of formula (Ie) are prepared from those of formula (Id) by saponification of the ester functional group in the presence of a base such as sodium or lithium hydroxide in an alcoholic solvent or in THF.

The compounds of formula (If) are obtained from the compound of formula (7) by lithiation with lithium diisopropylamide and then reaction with paraformaldehyde in an organic solvent such as THF. From the α-hydroxymethyl ester derivative (9) obtained by protecting the alcohol functional group in the form of a substituted methyl ether (for example 2-methoxyethoxymethyl ether (MEM) or tetrahydropyranyl ether) and by saponifying the ester functional group (sodium or lithium hydroxide in an alcoholic solvent or in THP), the compound of formula (10) is obtained. The latter is coupled with the aniline of formula (6) either by means of the acid chloride or in the presence of dicyclohexylcarbodiimide and dimethylaminopyridine in a solvent such as THF or dichloramethane, and then liberation of the alcohol functional group in the presence of trimethylsilyl iodide or trifluoroacetic acid.

When $R_1$ represents the —COOH radical, the compounds are preferably prepared by protecting $R_1$ with a protecting or protective group of the allyl, benzyl or tert-butyl type. Transformation to the free form can then be carried out:

(a) in the case of a protective allyl group, by means of a catalyst such as certain transition metal complexes in the presence of a secondary amine, (b) in the case of a protective benzyl group, by debenzylation in the presence of hydrogen, by means of a catalyst such as palladium on carbon, (c) in the case of a protective tert-butyl group, by means of trimethylsilyl iodide.

The present invention also features therapeutic/pharmaceutical applications of the compounds of formula (I).

These compounds exhibit activity in the test for differentiation of mouse embryonic teratocarcinoma cells (F9) (*Cancer Research*, 43, p. 5268 (1983)) and/or in the test for inhibition of ornithine decarboxylase after induction with TPA in mice (*Cancer Research*, 38, p. 793–801 (1978)). These tests demonstrate the activities of the subject compounds for cell differentiation and proliferation applications, respectively.

The compounds according to the invention are particularly suitable in the following fields of therapy:

(1) for treating dermatological conditions associated with a keratinization disorder related to differentiation and to proliferation, especially for treating acne vulgaris or comedo-type, polymorphic or rosacea acnes, nodulocystic acne or acne conglobata, senile acnes, secondary acnes such as solar acne, acne medicamentosa or occupational acne;

(2) for treating other types of keratinization disorders, especially ichthyoses, ichthyosiform states, Darier's disease, keratoses palmaris and plantaris, leucoplakias and leucoplakia-like states, skin or mucous (buccal) lichen;

(3) for treating other dermatological conditions associated with a keratinization disorder manifesting an inflammatory and/or immunoallergic component, and, especially, all forms of psoriasis, whether cutaneous, mucous or ungual, and even arthropathic psoriasis, or, alternatively, skin atopy, such as eczema or respiratory atopy or alternatively gingival hypertrophy; the compounds can also be used for treating inflammatory conditions not exhibiting keratinization disorder;

(4) for treating all dermal or epidermal proliferations, whether benign or malignant, whether or not they are of viral origin, such as verruca vulgaris, verruca plana and epidermodysplasia verruciformis, oral or florid papillomatoses and proliferations which can be induced by ultraviolet radiation, especially in the case of baso- and spinocellular epitheliomas;

(5) for treating other dermatological disorders such as bullous dermatoses and collagen diseases;

(6) for treating certain ophthalmological disorders, especially corneopathies;

(7) for repairing or combating skin aging, whether photoinduced or chronologic, or to reduce pigmentations and actinic keratoses, or all pathologies associated with chronologic or actinic aging;

(8) for preventing or curing the stigmas of epidermal and/or dermal atrophy induced by local or systolic corticosteroids, or any other form of skin atrophy;

(9) for preventing or treating cicatrization disorders or for preventing or for repairing vibices;

(10) for combating disorders of the sebaceous function, such as acne hyperseborrhoea or simple seborrhoea;

(11) for the treatment or prevention of cancerous or precancerous states;

(12) for the treatment of inflammatory conditions such as arthritis;

(13) for the treatment of any condition of viral origin at the level of the skin or in general;

(14) for the prevention or treatment of alopecia;

(15) for the treatment of dermatological or general conditions including an immunological component;

(16) for the treatment of conditions of the cardiovascular system, such as arteriosclerosis.

For the aforesaid therapeutic or pharmaceutical applications, the compounds according to the invention can advantageously be used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers. By "D vitamins or derivatives thereof" are intended, for example, the derivatives of vitamin $D_2$ or $D_3$ and in particular 1,25-dihydroxyvitamin $D_3$. By "anti-free radical agents" are intended, for example, α-tocopherol, superoxide dismutase, ubiquinol or certain metal-chelating agents. By "α-hydroxy or α-keto acids or derivatives thereof" are intended, for example, lactic, malic, citric, glycolic, mandelic, tartaric, glyceric or ascorbic acids or salts, amides or esters thereof. By "ion channel blockers" are intended, for example, minoxidil (2,4-diamino-6-piperidinopyrimidine 3-oxide) and derivatives thereof.

The present invention thus also features medicinal compositions containing at least one compound of formula (I), one of its optical or geometric isomers, or one of its pharmaceutically acceptable salts or other derivatives thereof.

The pharmaceutical/therapeutic compositions of this invention, intended especially for the treatment of the aforesaid disease states comprise a carrier which is pharmaceutically acceptable and compatible with the mode or regime of administration selected for the given composition, at least one compound of formula (I), one of its optical or geometric isomers or one of the salts, etc., thereof.

The administration of the compounds according to the invention can be carried out systemically, enterally, parenterally, topically or ocularly.

For enteral administration, the medicinal/pharmaceutical compositions may be in the form of tablets, gelatin capsules, sugar-coated tablets, syrups, suspensions, solutions, elixirs, powders, granules, emulsions, microopheres or nanospheres or lipid or polymeric vesicles which permit a controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the regime or rate of 1 to 3 doses per diem.

For topical administration, the pharmaceutical compositions based on compounds according to the invention are more particularly intended for the treatment of the skin and the mucous membranes and can be provided in the form of ointments, creams, milks, pommades, powders, impregnated pads, solutions, gels, sprays, lotions or suspensions. They may also be provided in the form of microopheres or nanospheres or lipid or polymeric vesicles or polymeric patches and hydrogels which permit a controlled release.

These compositions for topical administration may, moreover, be provided either in anhydrous form or in an aqueous form according to the particular clinical indication.

For ocular administration, they are principally collyria.

These compositions for topical or ocular application contain at least one compound of formula (I), or one of its optical or geometric isomers or, alternatively, one of its salts, etc., at a concentration preferably ranging from 0.001% to 5% by weight relative to the total weight of the composition.

The compounds of formula (I) according to the invention also find application in the cosmetic field, in particular for body and hair care and especially for the treatment of skins with acne tendency, for hair regrowth, against loss, for combating the greasy appearance of the skin or the hair, in the protection against the harmful effects of the sun or in the treatment of physiologically dry skins, for preventing and/or for combating photoinduced or chronologic ageing.

For cosmetic applications, the compositions of the invention may, moreover, be advantageously used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers, all of these different active agents being as defined above.

The present invention therefore also features cosmetic compositions comprising a carrier which is cosmetically acceptable and suitable for a topical application, at least one compound of formula (I) or one of its optical or geometric isomers or one of its salts.

Such cosmetic compositions are advantageously presented in the form of a cream, a milk, a lotion, a gel, microspheres or nanospheres or lipid or polymeric vesicles, a soap or a shampoo.

The concentration of the compound of formula (I) in the cosmetic compositions according to the invention advantageously ranges from 0.001% to 3% by weight relative to the total composition.

The medicinal and cosmetic compositions according to the invention may, in addition, contain inert or even pharmacodynamically or cosmetically active additives or combinations of these additives, and, especially: wetting agents; depigmenting agents such as hydroquinone, azelaic acid, caffeic acid or kojic acid; emollients; moisturizing agents such as glycerol, PEG 400, thiamorpholinone and its derivatives or alternatively urea; antiseborrhoeic or antiacne agents such as S-carboxymethylcysteine, S-benzylcysteamine, salts or derivatives thereof, benzoyl peroxide; antibiotics such as erythromycin and esters thereof, neomycin, clindamycin and esters thereof, tetracyclines; antifungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine-1,1- dioxide) and Phenytoin (5,4-diphenyl-2,4-imidazolidinedione); non-steroidal anti-inflammatory agents; carotenoids and especially :-carotene; anti-psoriatic agents such as anthralin and derivatives thereof; and, lastly, 5,8,11,14-eicosatetraynoic and 5,8,11-eicosatrynoic acids and esters and amides thereof.

The compositions according to the invention may also contain taste- or flavor-enhancing agents, preservatives such as parahydroxybenzoic acid esters, stabilizing agents, moisture regulating agents, pH regulating agents, osmotic pressure modifying agents, emulsifying agents, UV-A and UV-B screening agents, antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

EXAMPLE 1

Preparation of 4-[α-amino-(5,6,7,8-tetrahydro-5,5,8,8-tetramethyl-2-naphthyl)acetamido]benzoic acid:

(a) Preparation of 4-(5,6,7,8-tetrahydro-5,5,8,8-tetramethyl-2-naphthyl)-2,5-imidazolinedione:

21.6 g (0.1 mol) of 5,6,7,8-tetrahydro-5,5,8,8-tetramethyl-2-naphthaldehyde and 350 ml of ethanol were introduced into a three-necked flask. A solution of 14.7 g (0.3 mol) of sodium cyanide and 38.4 g (0.4 mol) of ammonium carbonate in 350 ml of water was added and the mixture was heated at 50° C. for 6 hours. The reaction medium was concentrated to 300 ml by evaporation under reduced pressure and then extracted with ethyl ether. The organic phase was decanted off, washed with water, dried over magnesium sulfate and evaporated. 24.9 g (87%) of the intended compound of melting point 213°–214° C. were recovered.

(b) Preparation of 5,6,7,8-tetrahydro-5,5,8,8-tetramethyl-2-naphthylglycine:

A solution of 12.9 g (0.045 mol) of the compound prepared in reaction (a) in 200 ml of 16% (w/v) sodium hydroxide was heated at reflux for 12 hours. The reaction medium was cooled, extracted with ethyl acetate, and the aqueous phase was acidified to pH 5.5 with concentrated hydrochloric acid. The solids which had precipitated were filtered, washed with ethyl acetate and dried over $P_2O_5$. 7.5 g (64%) of 5,6,7,8-tetrahydro-5,5,8,8-tetramethyl-2-naphthylglycine of melting point >360° C. were recovered.

(c) Preparation of N-(tert-butoxycarbonyl)-5,6,7,8-tetrahydro-5,5,8,8-tetramethyl-2-naphthylglycine:

6.3 g (24 mmol) of 5,6,7,8-tetrahydro-5,5,8,8-tetramethyl-2-naphthylglycine, 25 ml of TEF and 50 ml of NaOH (1N) were introduced into a round-bottomed flask. 15 g (70 mmol) of di-tert-butyl dicarbonate were added and the mixture was stirred at room temperature for 12 hours. The reaction medium was extracted with ethyl ether (3×100 ml), the aqueous phase was recovered, acidified to pH 2 with concentrated hydrochloric acid, and extracted with ethyl ether. The organic phase decanted off, washed with water, dried over magnesium sulfate and evaporated. 7.1 g (82%) of the intended compound were recovered.

d) Preparation of benzyl 4-[α-tert-butoxycarboxamido-(5,6,7,8-tetrahydro-5,5,8,8-tetramethyl-2-naphthyl)-acetamido]benzoate:

6.1 g (16.9 mmol) of N-(tert-butoxycarbonyl)-5,6,7,8-tetrahydro-5,5,8,8-tetramethyl-2-naphthylglycine, 3.8 g (16,9 mmol) of benzyl 4-aminobenzoate and 50 ml of THF were introduced into a round-bottomed flask, 3.5 g (16.9 mmol) of 1,3-dicyclohexylcarbodiimide and 2.1 g (16.9 mmol) of 4-dimethylaminopyridine were added successively and the mixture was stirred at room temperature for 4 hours. The reaction medium was poured into water, extracted with ethyl ether, the organic phase decanted off, dried over magnesium sulfate and evaporated. The residue obtained was purified by chromatography on a silica column eluted with a mixture of dichloromethane and hexane (80/20). 6.1 g (64%) of the intended ester were recovered.

(e) Preparation of benzyl 4-[α-amino-(5,6,7,8-tetrahydro-5,5,8,8-tetramethyl-2-naphthyl)acetamido]benzoate:

5 g (8.7 mmol) of the preceding compound prepared in (d) and 50 ml of dichloromethane were introduced into a round-bottomed flask. The mixture was cooled on ice and 1.25 ml (8.7 mmol) of trimethylsilyl iodide were added dropwise and the mixture was stirred at room temperature for 2 hours. The reaction medium was poured into ice, extracted with ethyl ether, the organic phase decanted off, dried over magnesium sulfate and evaporated. The residue obtained was triturated in 100 ml of a hexane-ethyl ether mixture (90-10), filtered and dried. 4.1 g (99%) of the intended compound of melting point 1960–197° C. were recovered.

(f) Synthesis of 4-[α-amino-(5,6,7,8-tetrahydro-5,5,8,8-tetramethyl-2-naphthyl)acetamido]benzoic acid:

2.9 g (6.1 mmol) of the ester prepared in (e), 50 ml of THF and 150 ml of a methanolic sodium hydroxide solution (2N) were introduced into a round-bottomed flask and the mixture was heated at reflux for 2 hours. The reaction medium was evaporated to dryness, the residue taken up in water, and acidified to pH 5 with hydrochloric acid. The solids which had precipitated were filtered, washed with water and dried over $P_2O_5$. 1.9 g (83%) of 4-[α-amino-(5,6,7,8-tetrahydro-5,5,8,8-tetramethyl-2-naphthyl)acetamido]benzoic acid of melting point 203°–204° C. were recovered.

EXAMPLE 2

Preparation of 4-[α-methoxyimino-(5,6,7,8-tetrahydro-5,5,8,8-tetramethyl-2-naphthyl)acetamido]benzoic acid:

(a) Preparation of allyl 4-[α-methoxyimino-(5,6,7,8-tetrahydro-5,5,8,8-tetramethyl-2-naphthyl)acetamido]benzoate:

1.7 g (4 mmol) of 4-(5,6,7,8-tetrahydro-5,5,8,8-tetramethyl-2-naphthylglyoxyloyloxy)benzoate (prepared as described in WO-92/06948), 100 ml of ethanol, 1 g (12 mmol) of methoxyamine hydrochloride and 120 ml of NaOH (IN) were introduced into a round-bottomed flask. The mixture was heated at reflux for 12 hours, the reaction medium evaporated, the residue taken up in water, and extracted with ethyl ether. The organic phase was decanted, dried over magnesium sulfate and evaporated. The residue obtained was purified by chromatography on a silica column eluted with a dichloromethane/hexane mixture (50/50). After evaporation of the solvents, 1.5 g (84%) of the expected ester were recovered.

(b) Synthesis of 4-[α-methoxyimino-(5,6,7,8-tetrahydro-5,5,8,8-tetramethyl-2-naphthyl)acetamido]benzoic acid:

1.4 g (3.1 mmol) of the ester prepared in (a), 190 mg (0.16 mmol) of tetrakis(triphenylphosphine)-palladium(O) and 50 ml of TEF were introduced into a three-necked flask under a nitrogen stream. 2.7 ml (31 mmol) of morpholine were then added dropwise and the mixture was stirred at room temperature for 2 hours. The reaction medium was evaporated to dryness, taken up in water, acidified to pH 1, and extracted with ethyl ether, the organic phase was decanted off, washed with water, dried over magnesium sulfate and evaporated. The residue obtained was triturated in 50 ml of dichloromethane, filtered and dried. 1.2 g (95%) of 4-[α-methoxyimino-(5,6,7,8-tetrahydro-5,5,8,8-tetramethyl-2-naphthyl)acetamido]benzoic acid of melting point 208°–209° C. were recovered.

EXAMPLE 3
Preparation of 4-[α-acetamido-(5,6,7,8-tetrahydro-5,5,8,8-tetramethyl-2-naphthyl)acetamido]benzoic acid:

(a) Preparation of benzyl 4-[α-acetamido-(5,6,7,8-tetrahydro-5,5,8,8-tetramethyl-2-naphthyl)acetamido] benzoate:

1.5 g (3.2 mmol) of benzyl 4-[α-amino-(5,6,7,8-tetrahydro-5,5,8,8-tetramethyl-2-naphthyl)acetamido] benzoate, 75 ml of THF and 490 μl (3.5 mmol) of triethylamine were introduced into a round-bottomed flask. 250 μl (3.5 mmol) of acetyl chloride were added dropwise and the mixture was stirred at room temperature for 2 hours. The reaction medium was poured into water, extracted with ethyl acetate, the organic phase decanted, dried over magnesium sulfate and evaporated. The residue obtained was triturated in hexane, filtered and dried. 1.6 g (94%) of the expected compound of melting point 258°–259° C. was obtained.

(b) Preparation of 4-[α-acetamido-(5,6,7,8-tetrahydro-5,5,8,8-tetramethyl-2-naphthyl)acetamido]benzoic acid:

Following the basic procedure of Example 1(f), beginning with 1 g (1.9 mmol) of benzyl 4-[α-acetamido-(5,6,7,8-tetrahydro-5,5,8,8-tetramethyl-2-naphthyl)acetamido] benzoate, 480 mg (58%) of the expected acid of melting point 197°–198° C. were obtained.

EXAMPLE 4
Preparation of syn-4-[α-hydroxyimino-(5,6,7,8-tetrahydro-5,5,8,8-tetramethyl-2-naphthyl)acetamido]benzoic acid:

(a) Preparation of allyl 4-[α-hydroxyimino-(5,6,7,8-tetrahydro-5,5,8,8-tetramethyl-2-naphthyl)acetamido] benzoate:

1.7 g (4 mmol) of allyl 4-(5,6,7,8-tetrahydro-5,5,8,8-tetramethyl-2-naphthylglyoxyloyloxy)benzoate, 1.1 g (16 mmol) of hydroxylamine hydrochloride and 50 ml of ethanol were introduced into a round-bottomed flasks 16 ml of NaOH (N) were added dropwise and the mixture was heated at reflux for 4 hours. The reaction medium was evaporated to dryness, the residue taken up in water, and extracted with ethyl ether. The organic phase was decanted, dried over magnesium sulfate and evaporated. The residue obtained was chromatographed on a silica column eluted with a dichloromethane/ethyl ether mixture (98/2). After evaporation of the solvents, 1.6 g (94%) of the expected compound of melting point 176°–177° C. were obtained.

(b) Synthesis of syn-4-[α-hydroxyimino-(5,6,7,8-tetrahydro-5,5,8,8-tetramethyl-2-naphthyl)acetamido] benzoic acid:

Following the basic procedure of Example 2(b), beginning with 10 g (23 mmol) of the above ester, 5.6 g (62%) of the expected acid of melting point 265°–266° C. were obtained.

EXAMPLE 5
Preparation of anti-4-[α-hydroxyimino-(5,6,7,8-tetrahydro-5,5,8,8-tetramethyl-2-naphthyl)acetamido]benzoic acid:

3 g (7.6 mmol) of syn-4-[α-hydroxyimino-(5,6,7,8-tetrahydro-5,5,8,8-tetramethyl-2-naphthyl)acetamido] benzoic acid in 500 ml of methanol were introduced into a photochemical reactor and the mixture was stirred for 48 hours at room temperature while under irradiation (medium pressure Hanovia lamp, with no filter). The reaction medium was evaporated and the residue obtained was purified by chromatography on a silica column eluted with a dichloromethane/methanol mixture (90/10). After evaporation of the solvents, 1.2 g (40%) of anti-4-[α-hydroxyimino-(5,6,7,8-tetrahydro-5,5,8,8-tetramethyl-2-naphthyl) acetamido]benzoic acid of melting point 269°–270° C. was recovered.

EXAMPLE 6
Preparation of 4-[α-methoxycarbonyl-(5,6,7,8-tetrahydro-5,5,8,8-tetramethyl-2-naphthyl)acetamido]benzoic acid:

(a) Preparation of methyl 5,6,7,8-tetrahydro-5,5,8,8-tetramethyl-2-naphthylacetate:

15 g (0.06 mol) of 5,6,7,8-tetrahydro-5,5,8,8-tetramethyl-2-naphthylacetic acid, 150 ml of methanol and 1.6 ml of concentrated sulfuric acid were introduced into a round-bottomed flask. The mixture was heated at reflux for 4 hours, the reaction medium evaporated, taken up in water, and extracted with ethyl acetate. The organic phase was decanted off and dried over magnesium sulfate. 15.9 g (99%) of the expected ester of melting point 83°–85° C. were recovered.

(b) Preparation of α-methoxycarbonyl-(5,6,7,8-tetrahydro-5,5,8,8-tetramethyl-2-naphthyl)acetic acid:

2.1 ml (14.6 mmol) of diisopropylamine and 80 ml of TEP were introduced into a three-necked flask under a nitrogen stream. At −78° C., 5.8 ml (14.6 mmol) of n-butyllithium (2.5M) were added dropwise, the mixture was stirred for 30 minutes, then a solution of 3.2 g (12.2 mmol) of methyl 5,6,7,8-tetrahydro-5,5,8,8-tetramethyl-2-naphthylacetate dissolved in 80 ml of THF was added dropwise and the mixture was stirred for one hour. While maintained at −78° C., $CO_2$ was introduced for minutes and then the temperature was permitted to increase to −40° C. and the reaction medium was poured into a 5N hydrochloric acid solution. The mixture was extracted with ethyl acetate, the organic phase decanted, dried over magnesium sulfate and evaporated. 3.7 g (100%) of expected acid were recovered in the form of a slightly yellow oil.

(c) Preparation of α-methoxycarbonyl-(5,6,7,8-tetrahydro-5,5,8,8-tetramethyl-2-naphthyl)acetic acid chloride:

3.1 g (0,01 mol) of the above acid, 30 ml of toluene and 0.2 ml of DMF were introduced into a round-bottomed flask and then the mixture was heated to 50° C. 900 μl (0.012 mol) of thionyl chloride were added dropwise and the mixture was heated at 80° C. for one hour. The reaction medium was evaporated to dryness and the crude acid chloride was recovered (100%), which acid was employed as is in the synthesis to follow.

(d) Preparation of allyl 4-[α-methoxycarbonyl-(5,6,7,8-tetrahydro-5,5,8,8-tetramethyl-2-naphthyl)acetamido] benzoate:

1.8 g (10 mmol) of allyl 4-aminobenzoate, 50 ml of THF and 1.7 ml (12 mmol) of triethylamine were introduced into a round-bottomed flask. A solution of 3.3 g (10 mmol) of α-methoxycarbonyl-(5,6,7,8-tetrahydro-5,5,8,8-tetramethyl-2-naphthyl)acetic acid chloride in 25 ml of THP was added dropwise and the mixture was stirred at room temperature for 2 hours. The reaction medium was poured into water, and extracted with ethyl acetate. The organic phase was decanted off, dried over magnesium sulfate and evaporated. The residue obtained was recrystallized from ethanol; 3.3 g (69%) of the expected compound of melting point 155°–56° C. were recovered after filtration and drying.

(e) Synthesis of 4-[α-methoxycarbonyl-(5,6,7,8-tetrahydro-5,5,8,8-tetramethyl-2-naphthyl)acetamido] benzoic acid:

Following the basic procedure of Example 2(b), beginning with 3.25 g (7 mmol) of the above allyl ester, 2,47 g (83%) of the expected acid of melting point 156°–157° C. were obtained.

EXAMPLE 7
Preparation of 4-[α-carboxy-(5,6,7,8-tetrahydro-5,5,8,8-tetramethyl-2-naphthyl)acetamido]benzoic acid:

Following the basic procedure of Example 1(f), beginning with 1.85 g (4 mmol) of allyl 4-[α-methoxycarbonyl-(5,6, 7,8-tetrahydro-5,5,8,8-tetramethyl-2-naphthyl)acetamido]benzoate, 1.2 g (74%) of 4-[α-carboxy-(5,6,7,8-tetrahydro-5,5,8,8-tetramethyl-2-naphthyl)acetamido]benzoic acid of melting point 213°–214° C. was obtained.

EXAMPLE 8

Preparation of 4-[α-carbamoyl-(5,6,7,8-tetrahydro-5,5,8,8-tetramethyl-2-naphthyl)acetamido]benzoic acid:

(a) Preparation of benzyl 5,6,7,8-tetrahydro-5,5,8,8-tetramethyl-2-naphthylacetate:

730 mg (0.024 mol) of sodium hydride (80 and 100 ml of DMF were introduced into a three-necked flank under a nitrogen stream. A solution of 5 g (0.02 mol) of 5,6,7,8-tetrahydro-5,5,8,8-tetramethyl-2-naphthylacetic acid in 40 ml of DMF was added dropwise and the mixture was stirred until the gaseous emission ceased. 2.9 ml (0.024 mol) of benzyl bromide were then added and the mixture was stirred at room temperature for 4 hours. The reaction medium was poured into water, and extracted with ethyl acetate. The organic phase was decanted off, dried over magnesium sulfate and evaporated. 6.7 g (100%) of the expected ester were recovered in the form of a slightly yellow oil.

(b) Preparation of α-benzyloxycarbonyl-(5,6,7,8-tetrahydro-5,5,8,8-tetramethyl-2-naphthyl)acetic acid:

Following the basic procedure of Example 6(b), beginning with 14 g (0.041 mol) of the above ester, 10.8 g (68%) of the expected compound were obtained in the form of a colorless oil.

(c) Preparation of α-benzyloxycarbonyl-(5,6,7,8-tetrahydro-5,5,8,8-tetramethyl-2-naphthyl)acetic acid chloride:

Following the basic procedure of Example 6(c), beginning with 5 g (13 mmol) of α-benzyloxycarbonyl-(5,6,7,8-tetrahydro-5,5,8,8-tetramethyl-2-naphthyl)acetic acid, 5.2 g (100%) of the crude acid chloride were obtained, which acid was employed as is in the synthesis to follow.

(d) Preparation of benzyl α-carbamoyl-(5,6,7,8-tetrahydro-5,5,8,8-tetramethyl-2-naphthyl) acetate:

125 ml of ammonium hydroxide (33%) were introduced into a round-bottomed flask, the mixture was cooled to 0° C. and a solution of 5.2 g (13 mmol) of the above acid chloride in 50 ml of ethyl ether was added dropwise and the mixture was stirred at room temperature for one hour. The reaction medium was poured into water, extracted with ethyl ether, the organic phase decanted off, dried over magnesium sulfate and evaporated. The residue obtained was recrystallized from an ethyl acetate/hexane mixture (30/70); 3.9 g (79%) of the expected compound of melting point 112°–113° C. were obtained.

(e) Preparation of α-carbamoyl-(5,6,7,8-tetrahydro-5,5,8,8-tetramethyl-2-naphthyl)acetic acid:

3.9 g (10 mmol) of benzyl α-carbamoyl-(5,6,7,8-tetrahydro-5,5,8,8-tetramethyl-2-naphthyl)acetate, 1.2 g of palladium on carbon (10%) and 100 ml of dioxane were introduced into a reactor. The mixture was hydrogenated at room temperature and at a pressure of 7 bar for 4 hours, filtered on celite and the filtrate evaporated to dryness. The residue obtained was taken up in the minimum amount of ethyl ether, filtered and dried. 2.2 g (76%) of the expected acid were recovered.

(f) Preparation of allyl 4-[α-carbamoyl-(5,6,7,8-tetrahydro-5,5,8,8-tetramethyl-2-naphthyl)acetamido]benzoate:

Following the basic procedure of Example 1(d), by reacting 2 g (6.9 mmol) of the above acid with 1.22 g (6.9 mmol) of allyl 4-aminobenzoate, 1.78 g (57%) of the expected ester of melting point 210°–211° C. was obtained.

(g) Synthesis of 4-[α-carbamoyl-(5,6,7,8-tetrahydro-5,5,8-tetramethyl-2-naphthyl)acetamido]benzoic acid:

Following the basic procedure of Example 2(b), beginning with 1.6 g (3.6 mmol) of allyl 4-[α-carbamoyl-(5,6,7,8-tetrahydro-5,5,8,8-tetramethyl-2-naphthyl)acetamido]benzoate, 690 mg (47%) of the expected acid of melting point 165°–167° C. were obtained.

EXAMPLE 9

Preparation of 2-hydroxy-4-[α-tert-butoxycarboxamido-(5,6,7,8-tetrahydro-5,5,8,8-tetramethyl-2-naphthyl)acetamido]benzoic acid:

5 (a) Preparation of allyl 2-hydroxy-4-[α-tert-butoxycarboxamido-(5,6,7,8-tetrahydro-5,5,8,8-tetramethyl-2-naphthyl)acetamido]benzoate:

Following the basic procedure of Example 1(d), by reacting 8 g (22 mmol) of N-(tert-butoxycarbonyl)-5,6,7,8-tetrahydro-5,5,8,8-tetramethyl-2-naphthylglycine prepared in Example 1(c) with 4.3 g (22 mmol) of allyl 2-hydroxy-4-aminobenzoate, 2.5 g (20%) of the expected allyl ester were obtained in the form of an oil.

(b) Synthesis of 2-hydroxy-4-[α-tert-butoxycarboxamido-(5,6,7,8-tetrahydro-5,5,8,8-tetramethyl-2-naphthyl)acetamido]benzoic acid:

Following the basic procedure of Example 2(b), beginning with 2.4 g (4.5 mmol) of allyl 2-hydroxy-4-[α-tert-butoxycarboxamido-(5,6,7,8-tetrahydro-5,5,8,8-tetramethyl-2-naphthyl)acetamido benzoate, 1.9 g (85%) of the expected acid of melting point 160°–165° C. was obtained.

EXAMPLE 10

Preparation of 2-hydroxy-4-[α-amino-(5,6,7,8-tetrahydro-5,5,8,8-tetramethyl-2-naphthyl)acetamido]benzoic acid:

1.52 g (3 mmol) of the above acid and 15 ml of dichloromethane were introduced into a round-bottomed flask, 880 μl (6 mmol) of trimethylsilyl iodide were added dropwise and the mixture was stirred at room temperature for 4 hours. The reaction medium was poured into water, and extracted with ethyl acetate. The organic phase was decanted off, washed with water, dried over magnesium sulfate and evaporated. The residue obtained was triturated in the minimum amount of ethyl ether, filtered and dried. 930 mg (77%) of the expected compound of melting point 240°–241° C. were recovered.

EXAMPLE 11

Preparation of 4-[α-methoxycarbonyl-(5,6,7,8-tetrahydro-5,5,8,8-tetramethyl-2-naphthyl)methylcarbamoyl]benzoic acid:

(a) Preparation of methyl 5,6,7,8-tetrahydro-5,5,8,8-tetramethyl-2-naphthylglycinate:

8 g (22 mmol) of 5,6,7,8-tetrahydro-5,5,8,8-tetramethyl-2-naphthylglycine and 100 ml of methanol were introduced into a round-bottomed flask and 9 ml (0.12 mol) of thionyl chloride were added dropwise. The mixture was stirred at room temperature for 12 hours, the reaction medium evaporated, and the residue taken up in sodium bicarbonate solution and ethyl ether. The organic phase was decanted off, dried over magnesium sulfate and evaporated. 6 g (100%) of the expected ester were recovered.

(b) Preparation of allyl 4-[α-methoxycarbonyl-(5,6,7,8-tetrahydro-5,5,8,8-tetramethyl-2-naphthyl)methylcarbamoyl]benzoate:

Following the basic procedure of Example 6(d), by reacting 1.1 g (4.8 mmol) of 4-allyloxycarbonylbenzoyl chloride (prepared according to WO-92/06948) with 1.2 g (4.4 mmol) of methyl 5,6,7,8-tetrahydro-5,5,8,8-tetramethyl-2-naphthylglycinate, 1.6 g (78%) of the expected allyl ester was obtained in the form of a slightly yellow oil.

(c) Synthesis of 4-[α-methoxycarbonyl-(5,6,7,8-tetrahydro-5,5,8,8-tetramethyl-2-naphthyl)methylcarbamoyl]benzoic acid:

Following the basic procedure of Example 2(b), beginning with 1.6 g (3.4 mmol) of allyl 4-[α-methoxycarbonyl-(5,6,7,8-tetrahydro-5,5,8,8-tetramethyl-2-naphthyl)methylcarbamoyl]benzoate, 750 mg (52%) of the expected acid of melting point 95°–100° C. were obtained.

EXAMPLE 12

Preparation of 4-[α-carboxyl-(5,6,7,8-tetrahydro-5,5,8,8-tetramethyl-2-naphthyl)methylcarbonyl]benzoic acid:

Following the basic procedure of Example 1(f), beginning with 1.1 g (2.2 mmol) of allyl 4-[α-methoxycarbonyl-(5,6,7,8-tetrahydro-5,5,8,8-tetramethyl-2-naphthyl)methylcarbamoyl]benzoate, 860 mg (92%) of the expected acid of melting point 180°–185° C. were obtained.

EXAMPLE 13

Preparation of 4-[α-hydroxymethyl -(5,6,7,8-tetrahydro-5,5,8,8-tetramethyl-2-naphthyl)methylcarbamoyl]benzoic acid:

(a) Preparation of 2-tert-butoxycarboxamido-2-(5,6,7,8-tetrahydro-5,5,8,8-tetramethyl-2-naphthyl)ethanol:

38 g (0.105 mol) of N-(tert-butoxycarbonyl)-5,6,7,8-tetrahydro-5,5,8,8-tetramethyl-2-naphthylglycine [prepared in Example 1(c)], 14.7 ml (0.105 mol) of triethylamine and 160 ml of THF were introduced into a three-necked flask under a nitrogen stream. The mixture was cooled at 0° C. and 9.9 ml (0.105 mol) of ethyl chloroformate were added dropwise and the mixture stirred at room temperature for 30 minutes. A solution of 9.9 g (0.262 mol) of sodium borohydride in 200 ml of water was then introduced and the mixture was stirred at room temperature for 2 hours. The reaction medium was poured into ice, extracted with ethyl acetate, the organic phase decanted off, dried over magnesium sulfate and evaporated. The solid obtained were triturated in hexane, filtered, dried and 26 g (72%) of 2-tert-butoxycarboxamido-2-(5,6,7,8-tetrahydro-5,5,8,8-tetramethyl-2-naphthyl)ethanol of melting point 119°–121° C. were recovered.

(b) Preparation of allyl 4-{[2-tert-butoxycarboxamido-2-(5,6,7,8-tetrahydro-5,5,8,8-tetramethyl-2-naphthyl)ethoxy]-carbonyl}-benzoate:

Following the basic procedure of Example 6(d), by reacting 1.1 g (3.1 mmol) of the above alcohol with 690 mg (3.4 mmol) of 4-allyloxycarbonylbenzoyl chloride, 1.36 g (85%) of allyl 4-{[2-tert-butoxycarboxamido-2-(5,6,7,8-tetrahydro-5,5,8,8-tetramethyl-2-naphthyl)ethoxy carbonyl}benzoate was obtained.

(c) Preparation of allyl 4-[α-hydroxymethyl-(5,6,7,8-tetrahydro-5,5,8,8-tetramethyl-2-naphthyl)methylcarbamoyl]benzoate:

4 g (7.5 mmol) of the above ester and 40 ml of dichloromethane were introduced into a round-bottomed flask and 10 ml of trifluoroacetic acid were added dropwise. The mixture was stirred at room temperature for 8 hours, the reaction medium evaporated and the allyl 4-{[2-amino-2-(5,6,7,8-tetrahydro-5,5,8,8-tetramethyl-2-naphthyl)ethoxy]carbonyl}benzoate was recovered.

This compound, by heating to 70° C. in 50 ml of toluene, was rearranged and 1.07 g (33%) of allyl 4-[α-hydroxymethyl-(5,6,7,8-tetrahydro-5,5,8,8-tetramethyl-2-naphthyl)methylcarbamoyl]benzoate of melting point 140°–145° C. was obtained.

(d) Synthesis of 4-[α-hydroxymethyl-(5,6,7,8-tetrahydro-5,5,8,8-tetramethyl-2-naphthyl)methylcarbamoyl]benzoic acid:

Following the basic procedure of Example 2(b), beginning with 1.05 g (2.5 mmol) of the above allyl ester, 660 mg (69%) of the expected acid of melting point 145°–150° C. were obtained.

EXAMPLE 14

Preparation of 4-[α-acetoxymethyl-(5,6,7,8-tetrahydro-5,5,8,8-tetramethyl-2-naphthyl)methylcarbamoyl]benzoic acid:

(a) Preparation of allyl 4-[α-acetoaxymethyl-(5,6,7,8-tetrahydro-5,5,8,8-tetramethyl-2-naphthyl)methylcarbamoyl]benzoate:

395-mg (0.9 mmol) of allyl 4-[α-hydroxymethyl-(5,6,7,8-tetrahydro-5,5,8,8-tetramethyl-2-naphthyl)methylcarbamoyl]benzoate, 15 ml of pyridine and 200 μl (1.8 mmol) of acetic anhydride were introduced into a round-bottomed flask. The mixture was stirred at room temperature for 8 hours, the reaction medium was poured into water, and extracted with ethyl ether. The organic phase was decanted off, washed with water, dried over magnesium sulfate and evaporated. 435 mg (100%) of the expected compound were recovered in the form of a colorless oil.

(b) Synthesis of 4-[α-acetoxymethyl-(5,6,7,8-tetrahydro-5,5,8,8-tetramethyl-2-naphthyl)methylcarbamoyl]benzoic acid:

Following the basic procedure of Example 2(b), beginning with 606 mg (1.27 mmol) of allyl 4-[α-acetoxymethyl-(5,6,7,8-tetrahydro-5,5,8,8-tetramethyl-2-naphthyl)methylcarbamoyl]benzoate, 347 mg (60%) of the expected acid of melting point 95°–100° C. were obtained.

EXAMPLE 15

Preparation of syn-4-[α-propyloxyimino-(5,6,7,8-tetrahydro-5,5,8,8-tetramethyl-2-naphthyl)acetamido] benzoic acid:

(a) Preparation of allyl syn-4-[α-propyloxyimino-(5,6,7,8-tetrahydro-5,5,8,8-tetramethyl-2-naphthyl)acetamido] benzoate:

2.2 g (5 mmol) of allyl 4-[α-hydroxyimino-(5,6,7,8-tetrahydro-5,5,8,8-tetramethyl-2-naphthyl)acetamido] benzoate [prepared in Example 4(a)], 700 mg (5 mmol) of potassium carbonate and 100 ml of methyl ethyl ketone were introduced into a three-necked flask under a nitrogen stream. 490 μl (5 mmol) of 1-iodopropane were added and the mixture was heated at reflux for two hours. The mixture was evaporated to dryness, taken up in water and ethyl ether, the organic phase decanted off, dried over magnesium sulfate and evaporated. The residue obtained was purified by chromatography on a silica column eluted with hexane. There were recovered 1.4 g (59%) of allyl syn-4-[α-propyloxyimino-(5,6,7,8-tetrahydro-5,5,8,8-tetramethyl-2-naphthyl)acetamido]benzoate in the form of a colorless oil and 230 mg (10%) of allyl anti-4-[α-propyloxyimino-(5,6,7,8-tetrahydro-5,5,8,8-tetramethyl--2-naphthyl)acetamido] benzoate of melting point 120°–21° C.

(b) Synthesis of syn-4-[α-propyloxyimino-(5,6,7,8-tetrahydro-5,5,8,8-tetramethyl-2-naphthyl)acetamido] benzoic acid:

1.2 g (2.5 mmol) of allyl syn-4-[α-propyloxyimino-(5,6,7,8-tetrahydro-5,5,8,8-tetramethyl-2-naphthyl)acetamido] benzoate, 100 ml of THF and 100 mg (0.08 mmol) of tetrakis (triphenylphosphine)palladium(O) were introduced into a three-necked flask under a nitrogen stream. 1.1 ml (12.5 mmol) of morpholine was then added dropwise and the mixture was stirred at room temperature for 2 hours. The reaction medium was evaporated to dryness, taken up in water, acidified to pH 1 and extracted with ethyl ether. The organic phase was decanted off, washed with water, dried over magnesium sulfate and evaporated. The residue obtained was purified by chromatography on a silica column eluted with dichloromethane. After evaporation of the solvents, 820 mg (75%) of syn-4-[α-propyloxyimino-(5,6,7,8-tetrahydro-5,5,8,8-tetramethyl-2-naphthyl)acetamido]benzoic acid of melting point 204°–205° C. were recovered.

EXAMPLE 16

Preparation of anti-4-[α-propyloxyimino-(5,6,7,8-tetrahydro-5,5,8,8-tetramethyl-2-naphthyl)acetamido]benzoic acid:

Following the basic procedure of Example 15(b), beginning with 200 mg (0.4 mmol) of allyl anti-4-[α-propyloxyimino-(5,6,7,8-tetrahydro-5,5,8,8-tetramethyl-2-naphthyl)acetamido]benzoate prepared in Example 15(a), 130 mg (71%) of anti-4-[α-propyloxyimino-(5,6,7,8-tetrahydro-5,5,8,8-tetramethyl-2-naphthyl)acetamido]benzoic acid of melting point 215°–217° C. were obtained.

EXAMPLE 17

Preparation of syn-4-[α-hexyloxyimino-(5,6,7,8-tetrahydro-5,5,8,8-tetramethyl-2-naphthyl)acetamido]benzoic acid:

(a) Preparation of allyl syn-4-[α-hexyloxyimino-(5,6,7,8-tetrahydro-5,5,8,8-tetramethyl-2-naphthyl)acetamido]benzoate:

Following the basic procedure of Example 15(a), by reacting 2.2 g (5 mmol) of allyl 4-[α-hydroxyimino-(5,6,7,8-tetrahydro-5,5,8,8-tetramethyl-2-naphthyl)acetamido]benzoate with 750 µl (5 mmol) of 1-iodohexane, there were obtained after chromatography on a silica column eluted with a mixture of dichloromethane and hexane (20/80), 1.6 g (62%) of allyl syn-4-[α-hexyloxyimino-(5,6,7,8-tetrahydro-5,5,8,8-tetramethyl-2-naphthyl)acetamido]benzoate in the form of a yellow oil and 420 mg (16%) of allyl anti-4-[α-hexyloxyimino-5,6,7,8-tetrahydro-5,5,8,8-tetramethyl-2-naphthyl)acetamido]benzoate in the form of a yellow oil.

(b) Synthesis of syn-4-[α-hexyloxyimino-(5,6,7,8-tetrahydro-5,5,8,8-tetramethyl-2-naphthyl)acetamido]benzoic acid:

Following the basic procedure of Example 15(b), beginning with 1.5 g (2.9 mmol) of allyl syn-4-[α-hexyloxyimino-(5,6,7,8-tetrahydro-5,5,8,8-tetramethyl-2-naphthyl)acetamido]benzoate, 1.1 g (79%) of syn-4-[α-hexyloxyimino-(5,6,7,8-tetrahydro-5,5,8,8-tetramethyl-2-naphthyl)acetamido]benzoic acid of melting point 188°–190° C. were obtained.

EXAMPLE 18

Preparation of anti-4-[α-hexyloxyimino-(5,6,7,8-tetrahydro-5,5,8,8-tetramethyl-2-naphthyl)acetamido]benzoic acid:

Following the basic procedure of Example 15(b), beginning with 400 mg (0.77 mmol) of allyl anti-4-[α-hexyloxyimino-(5,6,7,8-tetrahydro-5,5,8,8-tetramethyl-2-naphthyl)acetamido]benzoate prepared in Example 17(a), 250 mg (68%) of anti-4-[α-hexyloxyimino-(5,6,7,8-tetrahydro-5,5,8,8-tetramethyl-2-naphthyl)acetamido]benzoic acid of melting point 154°–156° C. were obtained.

EXAMPLE 19

Preparation of syn-4-[α-heptyloxyimino-(5,6,7,8-tetrahydro-5,5,8,8-tetramethyl-2-naphthyl)acetamido]benzoic acid:

(a) Preparation of allyl syn-4-[α-heptyloxyimino-(5,6,7,8-tetrahydro-5,5,8,8-tetramethyl-2-naphthyl)acetamido]benzoate:

Following the basic procedure of Example 15(a), by reacting 3.25 g (7.5 mmol) of allyl 4-[α-hydroxyimino-(5,6,7,8-tetrahydro-5,5,8,8-tetramethyl-2-naphthyl)acetamido]benzoate with 1.2 ml (7.5 mmol) of 1-iodoheptane, there were obtained after chromatography on a silica column eluted with a mixture of dichloromethane and hexane (50/50), 2 g (50%) of allyl syn-4-[α-heptyloxyimino-(5,6,7,8-tetrahydro-5,5,8,8-tetramethyl-2-naphthyl)acetamido]benzoate in the form of a colorless oil and 600 mg (15%) of allyl anti-4-[α-heptyloxyimino-(5,6,7,8-tetrahydro-5,5,8,8-tetramethyl-2-naphthyl)acetamido]benzoate in the form of a yellow oil.

(b) Synthesis of syn-4-[α-heptyloxyimino-(5,6,7,8-tetrahydro-5,5,8,8-tetramethyl-2-naphthyl)acetamido]benzoic acid:

Following the basic procedure of Example 15(b), beginning with 2 g (3.7 mmol) of allyl syn-4-[α-heptyloxyimino-(5,6,7,8-tetrahydro-5,5,8,8-tetramethyl-2-naphthyl)acetamido]benzoate, 1.5 g (81%) of syn-4-[α-heptyloxyimino-(5,6,7,8-tetrahydro-5,5,8,8-tetramethyl-2-naphthyl)acetamido]benzoic acid of melting point 178°–180° C. was obtained.

EXAMPLE 20

Preparation of anti-4-[α-heptyloxyimino-(5,6,7,8-tetrahydro-5,5,8,8-tetramethyl-2-naphthyl)acetamido]benzoic acid:

Following the basic procedure of Example 15(b), beginning with 600 mg (1.1 mmol) of allyl anti-4-[α-heptyloxyimino-(5,6,7,8-tetrahydro-5,5,8,8-tetramethyl-2-naphthyl)acetamido]benzoate prepared in Example 19(a), 250 mg (45%) of anti-4-[α-heptyloxyimino-(5,6,7,8-tetrahydro-5,5,8,8-tetramethyl-2-naphthyl)acetamido]benzoic acid of melting point 174°–178° C. were obtained.

EXAMPLE 21

Preparation of syn-4-[α-nonyloxyimino-(5,6,7,8-tetrahydro-5,5,8,8-tetramethyl-2-naphthyl)acetamido]benzoic acid:

(a) Preparation of allyl syn-4-[α-nonyloxyimino-(5,6,7,8-tetrahydro-5,5,8,8-tetramethyl-2-naphthyl)acetamido]benzoate:

Following the basic procedure of Example 15(a), by reacting 3.25 g (7.5 mmol) of allyl 4-[α-hydroxyimino-(5,6,7,8-tetrahydro-5,5,8,8-tetramethyl-2-naphthyl)acetamido]benzoate with 1.5 ml (7.5 mmol) of 1-iodoheptane, there were obtained after chromatography on a silica column eluted with a mixture of dichloromethane and hexane (40/60), 2.8 g (67%) of allyl syn-4-[α-nonyloxyimino-(5,6,7,8-tetrahydro-5,5,8,8-tetramethyl-2-naphthyl)acetamido]benzoate in the form of a yellow oil and 600 mg (14%) of allyl anti-4-[α-nonyloxyimino-(5,6,7,8-tetrahydro-5,5,8,8-tetramethyl-2-naphthyl)acetamido]benzoate in the form of a yellow oil.

(b) Synthesis of syn-4-[α-nonyloxyimino-(5,6,7,8-tetrahydro-5,5,8,8-tetramethyl-2-naphthyl)acetamido]benzoic acid:

Following the basic procedure of Example 15(b), beginning with 2.8 g (5 mmol) of allyl syn-4-[α-nonyloxyimino-(5,6,7,8-tetrahydro-5,5,8,8-tetramethyl-2-naphthyl)acetamido]benzoate, 1.9 g (73%) of syn-4-[α-nonyloxyimino-(5,6,7,8-tetrahydro-5,5,8,8-tetramethyl-2-naphthyl)acetamido]benzoic acid of melting point 162°–163° C. was obtained.

EXAMPLE 22

Preparation of anti-4[α-nonyloxyimino-(5,6,7,8-tetrahydro-5,5,8,8-tetramethyl-2-naphthyl)acetamido]benzoic acid:

Following the basic procedure of Example 15(b), beginning with 600 mg (1 mmol) of allyl anti-4-[α- nonyloxyimino-(5,6,7,8-tetrahydro-5,5,8,8-tetramethyl-2-naphthyl)acetamido]benzoate prepared in Example 21(a), 65 mg (12%) of anti-4-[α-nonyloxyimino-(5,6,7,8-tetrahydro-5,5,8,8-tetramethyl-2-naphthyl)acetamido] benzoic acid of melting point 155°–158° C. were obtained.

EXAMPLE 23

Preparation of syn-4-[α-dodecyloxyimino-(5,6,7,8-tetrahydro-5,5,8,8-tetramethyl-2-naphthyl)acetamido] benzoic acid:

(a) Preparation of allyl syn-4-[α-dodecyloxyimino-(5,6,7,8-tetrahydro-5,5,8,8-tetramethyl-2-naphthyl)acetamido] benzoate:

Following the basic procedure of Example 15(a), by reacting 3 g (6.9 mmol) of allyl 4-(α-hydroxyimino-(5,6,7,8-tetrahydro-5,5,8,8-tetramethyl-2-naphthyl)acetamido] benzoate with 1.7 ml (6.9 mmol) of 1-bromododecane, there were obtained after chromatography on a silica column eluted with a mixture of dichloromethane and heptane (30/70), 2.3 g (55%) of allyl syn-4-[α-dodecyloxyimino-(5,6,7,8-tetrahydro-5,5,8,8-tetramethyl-2-naphthyl)acetamido] benzoate in the form of a yellow oil.

(b) Synthesis of syn-4-[α-dodecyloxyimino-(5,6,7,8-tetrahydro-5,5,8,8-tetramethyl-2-naphthyl)acetamido] benzoic acid:

Following the basic procedure of Example 15(b), beginning with 2.3 g (3.8 mmol) of allyl syn-4-[α-dodecyloxyimino-(5,6,7,8-tetrahydro-5,5,8,8-tetramethyl-2-naphthyl)acetamido]benzoate, 1.4 g (65 of syn-4-[α-dodecyloxyimino-(5,6,7,8-tetrahydro-5,5,8,8-tetramethyl-2-naphthyl)acetamido]benzoic acid of melting point 165°–166° C. was obtained.

EXAMPLE 24

Preparation of methyl 5-[α-amino-(5,6,7,8-tetrahydro-5,5,8,8-tetramethyl-2-naphthyl)acetamido]-2-thiophenecarboxylate:

(a) Preparation of methyl 5-amino-2-thiophenecarboxylate:

3.6 g of iron powder, 1.4 g of $FeSO_4.7H_2O$, 25 ml of methanol and 8 ml of water were successively introduced into a three-necked flask. 940 mg (5 mmol) of methyl 5-nitro-2-thiophenecarboxylate were then added and the mixture was heated at 70° C. for eight hours. The reaction medium was filtered on celite, the filtrate evaporated, and taken up in water and ethyl ether. The organic phase was decanted, dried over magnesium sulfate and evaporated. The residue obtained was purified by chromatography on a silica column eluted with dichloromethane; 2 g (77%) of the expected compound of melting point 110°–112° C. were obtained.

(b) Preparation of methyl 5-[α-tert-butoxycarboxamido-(5,6,7,8-tetrahydro-5,5,8,8-tetramethyl-2-naphthyl) acetamido]-2-thiophenecarboxylate:

1.8 g (5 mmol) of N-(tert-butoxycarbonyl)-5,6,7,8-tetrahydro-5,5,8,8-tetramethyl-2-naphthylglycine, 780 mg (5 mmol) of methyl 5-amino-2-thiophenecarboxylate and 50 ml of THF were introduced into a round-bottomed flask. 1 g (5 mmol) of 1,3-dicyclohexylcarbodiimide and 610 mg (5 mmol) of 4-dimethylaminopyridine were successively added and the mixture was stirred at room temperature for 4 hours.

The reaction medium was poured into water, extracted with ethyl ether, the organic phase decanted, dried over magnesium sulfate and evaporated. The residue obtained was purified by chromatography on a silica column eluted with ethyl ether. 1.1 g (44%) of the expected ester of melting point 125°–126° C. was recovered.

(c) Synthesis of methyl 5-[α-amino-(5,6,7,8-tetrahydro-5,5,8,8-tetramethyl-2-naphthyl)acetamido]-2-thiophenecarboxylate:

1.1 g (2.2 mmol) of methyl 5-[α-tert-butoxycarboxamido-(5,6,7,8-tetrahydro-5,5,8,8-tetramethyl-2-naphthyl) acetamido]-2-thiophenecarboxylate and 50 ml of dichloromethane were introduced into a round-bottomed flask. The mixture was cooled on ice and 3.4 ml (44 mmol) of trifluoroacetic acid were added dropwise and the mixture was stirred at room temperature for 2 hours. The reaction medium was poured into ice, extracted with ethyl ether, the organic phase decanted, dried over magnesium sulfate and evaporated. The residue obtained was chromatographed on a silica column eluted with ethyl ether; 650 mg (74%) of methyl 5-[α-amino-(5,6,7,8-tetrahydro-5,5,8,8-tetramethyl-2-naphthyl)acetamido]-2-thiophenecarboxylate of melting point 177°–179° C. were obtained.

EXAMPLE 25

Preparation of methyl N-methyl-5-[α-amino-(5,6,7,8-tetrahydro-5,5,8,8-tetramethyl-2-naphthyl)acetamido]-2-pyrrolecarboxylate:

(a) Preparation of 2-trichloroacetylpyrrole:

45 g (247 mmol) of trichloroacetyl chloride and 100 ml of ethyl ether were introduced into a three-necked flask. A solution of 15.4 g (230 mmol) of pyrrole in 100 ml of ethyl ether was added dropwise and the mixture was stirred at room temperature for one hour and then a solution of 20 g of potassium carbonate in 60 ml of water was added slowly. The organic phase was decanted off, dried over magnesium sulfate, evaporated, the residue triturated in hexane and filtered. 42.7 g (87%) of the expected compound of melting point 78°–79° C. were recovered.

(b) Preparation of 5-nitro-2-trichloroacetylpyrrole:

21.3 g (0.1 mol) of 2-trichloroacetylpyrrole and 100 ml of acetic anhydride were introduced into a round-bottomed flask. At 0° C., a solution of 4.2 ml of fuming nitric acid, 8 ml of acetic acid and 8 ml of acetic anhydride was added dropwise and the temperature was permitted to increase to room temperature. The reaction medium was poured into ice, the pH adjusted to 8 with sodium bicarbonate, extracted with dichloromethane, the organic phase decanted off, dried over magnesium sulfate and evaporated. The residue obtained was purified by chromatography on a silica column eluted with a mixture of dichloromethane and hexane (60-40). There were recovered 5.5 g (21%) of 5-nitro-2-trichloroacetylpyrrole in the form of a dark green oil and 11.2 g of 4-nitro-2-trichloroacetylpyrrole of melting point 160°–163° C.

(c) Preparation of methyl 5-nitro-2-pyrrolecarboxylate:

5.5 g (21.3 mmol) of 5-nitro-2-trichloroacetylpyrrole and 100 ml of methanol were introduced into a round-bottomed flask and 3.6 g of sodium methoxide were added in small quantities. The mixture was stirred at room temperature for 2 hours, the reaction medium was evaporated, the residue was triturated in water, the solid filtered and dried. 3 g (83%) of the expected methyl ester of melting point 178°–179° C. were recovered.

(d) Preparation of methyl N-methyl-5-nitro-2-pyrrolocarboxylate:

220 mg (7.6 mmol) of sodium hydride (80% in oil) and 50 ml of DMF were introduced into a three-necked flask under a nitrogen stream. A solution of 1.3 g (7.6 mmol) of methyl 5-nitro-2-pyrrolecarboxylate in 50 ml of DMF was added dropwise and the mixture was stirred until the gaseous emission ceased. At 0° C., 480 μl (7.6 mmol) of iodomethane were then added and the mixture was stirred for four hours. The reaction medium was poured into water, extracted with ethyl ether, the organic phase decanted, dried over magnesium sulfate and evaporated. The residue obtained was triturated in hexane, filtered and dried. 1.3 g (92%) of the expected product of melting point 117°–118° C. was recovered.

(e) Preparation of methyl N-methyl-5-amino-2-pyrrolecarboxylate:

1.31 g (7.4 mmol) of methyl N-methyl-5-nitro-2-pyrrolecarboxylate, 400 mg of palladium on carbon (10%) and 50 ml of methanol were introduced into a reactor. The mixture was hydrogenated at room temperature and at a pressure of 7 bar for 2 hours. The catalyst was filtered, washed twice with 25 ml of methanol and the filtrates evaporated. 1.1 g (100%) of the expected amine was recovered in the form of a dark red oil.

(f) Preparation of methyl N-methyl-5-[α-tert-butoxycarboxamido-(5,6,7,8-tetrahydro-5,5,8,8-tetramethyl-2-naphthyl) acetamido]-2-pyrrolecarboxylate:

Following the basic procedure of Example 24(b), by reacting 2.6 g (7.13 mmol) of N-(tert-butoxycarbonyl)-5,6,7,8-tetrahydro-5,5,8,8-tetramethyl-2-naphthylglycine with 1.1 g (7.13 mmol) of methyl N-methyl-5-amino-2-pyrrolecarboxylate, 600 mg (17%) of the expected methyl ester of melting point 185°–187° C. were obtained.

(g) Synthesis of methyl N-methyl-5-[α-amino-(5,6,7,8-tetrahydro-5,5,8,8-tetramethyl-2-naphthyl)acetamido]-2-pyrrolecarboxylate:

480 mg (1 mmol) of methyl N-methyl-5-[α-tert-butoxycarboxamido-(5,6,7,8-tetrahydro-5,5,8,8-tetramethyl-2-naphthyl)acetamido]-2-pyrrolecarboxylate and 20 ml of dichloromethane were introduced into a round-bottomed flask. The mixture was cooled on ice and 170 μl (1.2 mmol) of trimethylsilyl iodide were added dropwise and the mixture was stirred at room temperature for 2 hours. The reaction medium was poured into ice, extracted with ethyl ether, the organic phase decanted, dried over magnesium sulfate and evaporated. The residue obtained was purified by chromatography on a silica column eluted with a mixture of ethyl acetate and heptane (70/30), 210 mg (53%) of methyl N-methyl-5-[α-amino-(5,6,7,8-tetrahydro-5,5,8,8-tetramethyl-2-naphthyl)acetamido]-2-pyrrolecarboxylate of melting point 143°–144° C. were recovered.

EXAMPLE 26

Preparation of methyl N-methyl-4-[α-amino-(5,6,7,8-tetrahydro-5,5,8,8-tetramethyl-2-naphthyl)acetamido]-2-pyrrolecarboxylate:

(a) Preparation of methyl 4-nitro-2-pyrrolecarboxylate:

Following the basic procedure of Example 25(c), beginning with 11.2 g (43.5 mmol) of 4-nitro-2-trichloroacetylpyrrole prepared in Example 25(b), 4.9 g (66%) of the expected methyl ester of melting point 196°–197° C. were obtained.

(b) Preparation of methyl N-methyl-4-nitro-2-pyrrolecarboxylate:

Following the basic procedure of Example 25(d), by reacting 2.9 g (17 mmol) of methyl 4-nitro-2-pyrrolecarboxylate with 1.1 ml of iodomethane, 2.8 g (89%) of the expected compound of melting point 122°–124° C. were obtained.

(c) Preparation of methyl N-methyl-4-amino-2-pyrrolocarboxylate:

Following the basic procedure of Example 25(e), beginning with 2.8 g (15.2 mmol) of methyl N-methyl-4-nitro-2-pyrrolecarboxylate, 2.3 g (100%) of the expected amine were obtained in the form of a chestnut-colored oil.

(d) Preparation of methyl N-methyl-4-[α-tert-butoxycarboxamido-(5,6,7,8-tetrahydro-5,5,8,8-tetramethyl-2-naphthyl)acetamido]-2-pyrrolecarboxylate:

Following the basic procedure of Example 24(b), by reacting 5.4 g (14.9 mmol) of N-(tert-butoxycarbonyl)-5,6,7,8-tetrahydro-5,5,8,8-tetramethyl-2-naphthylglycine with 2.3 g (14.9 mmol) of methyl N-methyl-4-amino-2-pyrrolecarboxylate, 3.58 g (50%) of the expected methyl ester were obtained.

(e) Synthesis of methyl N-methyl-4-[α-amino-(5,6,7,8-tetrahydro-5,5,8,8-tetramethyl-2-naphthyl)acetamido]-2-pyrrolecarboxylate:

Following the basic procedure of Example 25(g), beginning with 3.5 g (7.2 mmol) of methyl N-methyl-4-[α-tert-butoxycarboxamido-(5,6,7,8-tetrahydro-5,5,8,8-tetramethyl-2-naphthyl)acetamido]-2-pyrrolecarboxylate, 1.35 g (47%) of the expected product of melting point 220°–224° C. was obtained.

EXAMPLE 27

Preparation of methyl-N-propyl-4-[α-amino-(5,6,7,8-tetrahydro-5,5,8,8-tetramethyl-2-naphthyl)acetamido]-2-pyrrolecarboxylate:

(a) Preparation of methyl N-propyl-4-nitro-2-pyrrolecarboxylate:

Following the basic procedure of Example 25(d), by reacting 1.79 g (10.5 mmol) of methyl 4-nitro-2-pyrrolecarboxylate with 1.23 ml (12.6 mmol) of 3-iodopropane, 1.42 g (64%) of the expected compound was obtained.

(b) Preparation of methyl N-Propyl-4-amino-2-pyrrolecarboxylate:

Following the basic procedure of Example 25(e), beginning with 1.41 g (6.6 mmol) of methyl N-propyl-4-nitro-2-pyrrolecarboxylate, 1.18 g (100%) of the expected amine was obtained in the form of a chestnut colored oil.

(c) Preparation of methyl N-propyl-4-[α-tert-butoxycarboxamido-(5,6,7,8-tetrahydro-5,5,8,8-tetramethyl-2-naphthyl)acetamido]-2-pyrrolecarboxylate:

Following the basic procedure of Example 24(b), by reacting 2.34 g (6.5 mmol) of N-(tert-butoxycarbonyl)-5,6,7,8-tetrahydro-5,5,8,8-tetramethyl-2-naphthylglycine with 1.18 g (6.5 mmol) of methyl N-propyl-4-amino-2-pyrrolecarboxylate, 2.1 g of the expected methyl ester were obtained.

(d) Synthesis of methyl N-propyl-4-[α-amino-(5,6,7,8-tetrahydro-5,5,8,8-tetramethyl-2-naphthyl)acetamido]-2-pyrrolecarboxylate:

Following the basic procedure of Example 25(g), beginning with 2 g (3.8 mmol) of methyl N-propyl-4-[α-tert-butoxycarboxamido-(5,6,7,8-tetrahydro-5,5,8,8-tetramethyl-2-naphthyl) acetamido] -2-pyrrolecarboxylate, 820 mg (51%) of the expected compound of melting point 152°–153° C. were obtained.

EXAMPLE 28

Preparation of 4'-[α-amino-(5,6,7,8-tetrahydro-5,5,8,8-tetramethyl-2-naphthyl)acetamido]acetophenone:

(a) Preparation of 4'-[α-tert-butoxycarboxamido-(5,6,7,8-tetrahydro-5,5,8,8-tetramethyl-2-naphthyl) acetamido] acetophenone:

Following the basic procedure of Example 24(b), by reacting 1.8 g (5 mmol) of N-(tert-butoxycarbonyl)-5,6,7,8-tetrahydro-5,5,8,8-tetramethyl-2-naphthylglycine with 670 mg (5 mmol) of 4'-aminoacetophenone, 2.38 g (42%) of the expected compound of melting point 138°–139° C. were obtained.

(b) Synthesis of 4'-[α-amino-(5,6,7,8-tetrahydro-5,5,8,8-tetramethyl-2-naphthyl)acetamido]acetophenone:

Following the procedure of Example 24(c), beginning with 840 mg (1.7 mmol) of 4'-[α-tert-butoxycarboxamido- (5,6,7,8-tetrahydro-5,5,8,8-tetramethyl-2-naphthyl) acetamido]acetophenone, 580 mg (87%) of the expected compound of melting point 214°–215° C. were obtained.

EXAMPLE 29
Preparation of 4-[α-amino-(5,6,7,8-tetrahydro-5,5,8,8-tetramethyl-2-naphthyl)toluene:

(a) Preparation of 4-[α-tert-butoxycarboxamido-(5,6,7,8-tetrahydro-5,5,8,8-tetramethyl-2-naphthyl)acetamido]toluene:

Following the basic procedure of Example 24(b), by reacting 1.8 g (5 mmol) of N-(tert-butoxycarbonyl)-5,6,7,8-tetrahydro-5,5,8,8-tetramethyl-2-naphthylglycine with 530 mg (5 mmol) of 4-aminotoluene, 1 g (44%) of the expected compound of melting point 195°–196° C. was obtained.

(b) Synthesis of 4-[α-amino-(5,6,7,8-tetrahydro-5,5,8,8-tetramethyl-2-naphthyl)acetamido]toluene:

Following the basic procedure of Example 24(c), beginning with 700 mg (1.55 mmol) of 4-[α-tert-butoxycarboxamido-(5,6,7,8-tetrahydro-5,5,8,8-tetramethyl-2-naphthyl)acetamido]toluene, 300 mg (55 of the expected compound of melting point 161°–163° C. were obtained.

EXAMPLE 30
Preparation of 4-[α-amino-(5,6,7,8-tetrahydro-5,5,8,8-tetramethyl-2-naphthyl)phenyl sulfonylmethane:

(a) Preparation of 4-[α-tert-butoxycarboxamido-(5,6,7,8-tetrahydro-5,5,8,8-tetramethyl-2-naphthyl)acetamido]-phenylsulfonylmethane:

Following the basic procedure of Example 24(b), by reacting 1.8 g (5 mmol) of N-(tert-butoxycarbonyl)-5,6,7,8-tetrahydro-5,5,8,8-tetramethyl-2-naphthylglycine with 850 mg (5 mmol) of 4-aminophenylsulphonylmethane, 300 mg (12%) of the expected compound of melting point 156°–157° C. were obtained.

(b) Synthesis of 4'-[α-amino-(5,6,7,8-tetrahydro-5,5,8,8-tetramethyl-2-naphthyl)acetamido]phenylsulfonylmethane:

Following the basic procedure of Example 24(c), beginning with 300 mg (0.6 mmol) of 4-[α-tert-butoxycarboxamido-(5,6,7,8-tetrahydro-5,5,8,8-tetramethyl-2-naphthyl)acetamido]phenylsulfonylmethane, 45 mg (19%) of the expected compound of melting point 175°–176° C. were obtained.

EXAMPLE 31
Preparation of 4-[α-tert-butoxycarboxamido-(5,6,7,8-tetrahydro-5,5,8,8-tetramethyl-2-naphthyl)acetamido]-phenylcarboxamide:

Following the basic procedure of Example 24(b), by reacting 1.8 g (5 mmol) of N-(tert-butoxycarbonyl)-5,6,7,8-tetrahydro-5,5,8,8-tetramethyl-2-naphthylglycine with 680 mg (5 mmol) of 4-aminophenylcarboxamide, 1.5 g (63%) of 4-[α-tert-butoxycarboxamido-(5,6,7,8-tetrahydro-5,5,8,8-tetramethyl-2-naphthyl)acetamido]phenylcarboxamide of melting point >360° C. was obtained.

EXAMPLE 32
Preparation of 4'-[α-amino-(5,6,7,8-tetrahydro-5,5,8,8-tetramethyl-2-naphthyl)benzyl acetate:

(a) Preparation of 4-nitrobenzyl acetate:

7.6 g (0.05 mol) of 4-nitrobenzyl alcohol, 4.7 ml (0.05 mol) of acetic anhydride and 5.8 ml (0.1 mol) of acetic acid were introduced into a round-bottomed flask and the mixture was heated at reflux for eight hours. The reaction medium was poured into water, extracted with ethyl ether, the organic phase decanted off, dried over magnesium sulfate and evaporated. The residue was triturated in hexane, filtered and dried. 6.1 g (62%) of 4-nitrobenzyl acetate of melting point 77°–78° C. were recovered.

(b) Preparation of 4-aminobenzyl acetate:

Following the basic procedure of Example 25(e), beginning with 3 g (15.4 mmol) of 4-nitrobenzylacetate, 2.5 g (97%) of 4-aminobenzyl acetate of melting point 83°–84° C. were obtained.

(c) Preparation of 4'-[α-tert-butoxycarboxamido-5,6,7,8-tetrahydro-5,5,8,8-tetramethyl-2-naphthyl)acetamido] benzyl acetate:

Following the basic procedure of Example 24(b), by reacting 1.8 g (5 mmol) of N-(tert-butoxycarbonyl)-5,6,7,8-tetrahydro-5,5,8,8-tetramethyl-2-naphthylglycine with 820 mg (5 mmol) of 4-aminobenzyl acetate, 400 mg (16%) of the expected compound of melting point 209°–210° C. were obtained.

(d) Synthesis of 4'-[α-amino-(5,6,7,8-tetrahydro-5,5,8,8-tetramethyl-2-naphthyl)acetamido]benzyl acetate:

Following the basic procedure of Example 24(c), beginning with 2.3 g (4.5 mmol) of 4'-[α-tert-butoxycarboxamido-(5,6,7,8-tetrahydro-5,5,8,8-tetramethyl-2-naphthyl)acetamido]benzyl acetate, 1.3 g (71%) of the expected compound of melting point 185°–186° C. were obtained.

EXAMPLE 33
Preparation of syn-2-hydroxy-4-[α-hydroxyimino-(5,6,7,8-tetrahydro-5,5,8,8-tetramethyl-2-naphthyl)acetamido] benzoic acid:

(a) Preparation of allyl 2-hydroxy-4-(5,6,7,8-tetrahydro-5,5,8,8-tetramethyl-2-naphthoylcarboximido)benzoate:

A solution of 10.6 g (38 mmol) of 5,6,7,8-tetrahydro-5,5,8,8-tetramethyl-2-naphthylglyoxyloyl chloride (preparation described in WO-92/06948) in 50 ml of TEF was added dropwise to a solution of 7.33 g (38 mmol) of allyl 2-hydroxy-4-aminobenzoate, 9.2 ml of pyridine and 50 ml of THF and the mixture was stirred at room temperature for 4 hours. The reaction medium was poured into water, extracted with ethyl ether, the organic phase decanted off, dried over magnesium sulfate and evaporated. The residue obtained was purified by chromatography on a silica column eluted with a mixture of dichloromethane and heptane (40/60). 4.99 g (34%) of allyl 2-hydroxy-4-(5,6,7,8-tetrahydro-5,5,8,8-tetramethyl-2-naphthoylcarboxamido) benzoate of melting point 100°–101° C. were recovered.

(b) Preparation of allyl 2-hydroxy-4-[α-hydroxyimino-(5,6,7,8-tetrahydro-5,5,8,8-tetramethyl-2-naphthyl)acetamido] benzoate:

Following the basic procedure of Example 4(a), by reacting 4.6 g (10.5 mmol) of allyl 2-hydroxy-4-(5,6,7,8-tetrahydro-5,5,8,8-tetramethyl-2-naphthoylcarboxamido) benzoate with 2.3 g (42.2 mmol) of hydroxylamine hydrochloride, 2.5 g (53%) of the expected compound of melting point 108°–109° C. were obtained.

(c) Synthesis of syn-2-hydroxy-4-[α-hydroxyimino-(5,6,7,8-tetrahydro-5,5,8,8-tetramethyl-2-naphthyl)acetamido] benzoic acid:

Following the basic procedure of Example 2(b), beginning with 2 g (4.4 mmol) of allyl 2-hydroxy-4-[α-hydroxyimino-(5,6,7,8-tetrahydro-5,5,8,8-tetramethyl-2-naphthyl)acetamido]benzoate, there were obtained after chromatography on a silica column eluted with a mixture of dichloromethane and methanol (95/5), 310 mg (15%) of syn-2-hydroxy-4-[α-hydroxyimino-(5,6,7,8-tetrahydro-5,5,8,8-tetramethyl-2-naphthyl)acetamido]benzoic acid of melting point 240° C. with decomposition.

EXAMPLE 34

Preparation of 4-[2-ethoxycarbonyl-2-(5,6,7,8-tetrahydro-5,5,8,8-tetramethyl-2-naphthyl)acrylamido]benzoic acid:

(a) Preparation of 2-ethoxycarbonyl-2-(5,6,7,8-tetrahydro-5,5,8,8-tetramethyl-2-naphthyl)acrylic acid:

320 mg (11 mmol) of sodium hydride (80% in oil) and 20 ml of THF were introduced into a three-necked flask under a nitrogen stream, a solution of 2.2 ml (11 mmol) of triethylphosphonoacetate was added dropwise and the mixture was stirred until the gaseous emission ceased. This solution was added dropwise to a solution of 2.8 g (10 mmol) of the sodium salt of 5,6,7,8-tetrahydro-5,5,8,8-tetramethyl-2-naphthylglyoxylic acid in 50 ml of THF. The mixture was stirred at room temperature for 2 hours, the reaction medium was poured into 100 ml of 0.5N hydrochloric acid, extracted with ethyl ether, the organic phase decanted off, dried over magnesium sulfate and evaporated. The residue obtained was purified by chromatography on a silica column eluted with dichloromethane. 2 g (61%) of 2-ethoxycarbonyl-2-(5,6,7,8-tetrahydro-5,5,8,8-tetramethyl-2-naphthyl)acrylic acid of melting point 114°–116° C. were recovered.

(b) Preparation of allyl 4-[2-ethoxycarbonyl-2-(5,6,7,8-tetrahydro-5,5,8,8-tetramethyl-2-naphthyl)acrylamido]benzoate:

Following the basic procedure of Example 24(b), by reacting 2 g (6 mmol) of 2-ethoxycarbonyl-2-(5,6,7,8-tetrahydro-5,5,8,8-tetramethyl-2-naphthyl)acrylic acid with 1 g (6-mmol) of allyl 4-aminobenzoate, 650 mg (22%) of the expected allyl ester of melting point 116°–118° C. were obtained.

(c) Synthesis of 4-[2-ethoxycarbonyl-2-(5,6,7,8-tetrahydro-5,5,8,8-tetramethyl-2-naphthyl)acrylamido]benzoic acid:

Following the basic procedure of Example 15(b), beginning with 610 mg (1.2 mmol) of allyl 4-[2-ethoxycarbonyl-2-(5,6,7,8-tetrahydro-5,5,8,8-tetramethyl-2-naphthyl)acrylamido]benzoate, 360 mg (64%) of the expected acid of melting point 155°–157° C. were obtained.

EXAMPLE 35

Preparation of allyl 4-[2-tert-butoxycarbonyl-2-(5,6,7,8-tetrahydro-5,5,8,8-tetramethyl-2-naphthyl)acrylamido]benzoate:

(a) Preparation of 2-tert-butoxycarbonyl-2-(5,6,7,8-tetrahydro-5,5,8,8-tetramethyl-2-naphthyl)acrylic acid:

Following the basic procedure of Example 34(a), by reacting 14.8 g (52.3 mmol) of the sodium salt of 5,6,7,8-tetrahydro-5,5,8,8-tetramethyl-2-naphthylglyoxylic acid with 11.4 ml (52.3 mmol) of tert-butyl P,P-dimethylphosphonoacetate, 8.8 g (48%) of 2-tert-butoxycarbonyl-2-(5,6,7,8-tetrahydro-5,5,8,8-tetramethyl-2-naphthyl)acrylic acid of melting point 134°–136° C. were obtained.

(b) Synthesis of allyl 4-[2-tert-butoxycarbonyl-2-(5,6,7,8-tetrahydro-5,5,8,8-tetramethyl-2-naphthyl)-acrylamido]benzoate:

Following the basic procedure of Example 24(b), by reacting 4 g (11.1 mmol) of 2-tert-butoxycarbonyl-2-(5,6,7,8-tetrahydro-5,5,8,8-tetramethyl-2-naphthyl)acrylic acid with 2 g (11.2 mmol) of allyl 4-aminobenzoate, 1.1 g (20%) of the expected allyl ester of melting point 155°–157° C. was obtained.

EXAMPLE 36

In this example, various specific formulations based on the compounds according to the invention are illustrated.

(A) ORAL ROUTE (a) 0.2 g Tablet

| | |
|---|---|
| (i) Compound prepared in Example 1 | 0.001 g |
| (ii) Starch | 0.114 g |
| (iii) Dicalcium phosphate | 0.020 g |
| (iv) Silica | 0.020 g |
| (v) Lactose | 0.030 g |
| (vi) Talc | 0.010 g |
| (vii) Magnesium stearate | 0.005 g |

(b) Oral suspension in 5 ml ampoules

| | |
|---|---|
| (i) Compound prepared in Example 6 | 0.001 g |
| (ii) Glycerin | 0.500 g |
| (iii) Sorbitol at 70% | 0.500 g |
| (iv) Sodium saccharinate | 0.010 g |
| (v) Methyl parahydroxybenzoate | 0.040 g |
| (vi) Flavoring | qs |
| (vii) Purified water    qs | 5 ml |

(c) 0.8 g Tablet

| | |
|---|---|
| (i) Compound of Example 10 | 0.500 g |
| (ii) Pregelatinized starch | 0.100 g |
| (iii) Microcrystalline cellulose | 0.115 g |
| (iv) Lactose | 0.075 g |
| (v) Magnesium stearate | 0.010 g |

(d) Oral suspension in 10 ml ampoules

| | |
|---|---|
| (i) Compound of Example 4 | 0.200 g |
| (ii) Glycerin | 1.000 g |
| (iii) Sorbitol at 70% | 1.000 g |
| (iv) Sodium saccharinate | 0.010 g |
| (v) Methyl parahydroxybenzoate | 0.080 g |
| (vi) Flavoring | qs |
| (vii) Purified water    qs | 10 ml |

(B) TOPICAL ROUTE (a) Ointment

| | |
|---|---|
| (i) Compound of Example 1 | 0.020 g |
| (ii) Isopropyl myristate | 81.700 g |
| (iii) Fluid paraffin oil | 9.100 g |
| (iv) Silica ("Aerosil 200" marketed by DEGUSSA) | 9.100 g |

(b) Ointment

| | |
|---|---|
| (i) Compound of Example 10 | 0.300 g |
| (ii) Petroleum jelly | 100 g |

(c) Nonionic water-in-oil cream

| | |
|---|---|
| (i) Compound of Example 5 | 0.100 g |
| (ii) Mixture of emulsive lanolin alcohols, waxes and oils ("anhydrous Eucerin" marketed by BDF) | 39.900 g |
| (iii) Methyl parahydroxybenzoate | 0.075 g |
| (iv) Propyl parahydroxybenzoate | 0.075 g |
| (v) Sterile demineralized water    qs | 100 g |

(d) Lotion

| | |
|---|---|
| (i) Compound of Example 6 | 0.100 g |
| (ii) Polyethylene glycol (PEG 400) | 69.900 g |
| (iii) Ethanol at 95% | 30.000 g |

(e) Hydrophobic ointment

| | |
|---|---|
| (i) Compound of Example 7 | 0.300 g |
| (ii) Isopropyl myristate | 36.400 g |
| (iii) Silicone oil ("Rhodorsil 47 V 300" marketed by RHONE-POULENC) | 36.400 g |
| (iv) Beeswax | 13.600 g |
| (v) Silicone oil ("Abil 300.000 cst" marketed by GOLDSCHMIDT) | 100 g |

(f) Nonionic oil-in-water cream

| | |
|---|---|
| (i) Compound of Example 10 | 1.000 g |

-continued

| | |
|---|---|
| (ii) Cetyl alcohol | 4.000 g |
| (iii) Glycerol monostearate | 2.500 g |
| (iv) PEG 50 stearate | 2.500 g |
| (v) Shea butter | 9.200 g |
| (vi) Propylene glycol | 2.000 g |
| (vii) Methyl parahydroxybenzoate | 0.075 g |
| (viii) Propyl parahydroxybenzoate | 0.075 g |
| (ix) Sterile demineralized water | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polyaromatic amide compound having the structural formula (I):

(I)

in which Z represents —CO—NH— or —NH—CO—; Ar is a radical selected from among those of the following formulae (b) and (e):

(a)

(b)

(c)

(d)

(e)

wherein $R_5$ and $R_6$ are as defined below; $R_1$ is (i) a radical —$CH_3$, (ii) a radical —$CH_2$—O—$R_6$, (iii) a radical —O—$R_6$, (iv) a radical —CO—$R_7$, or (v) a radical —S(O)$_t$ $R_9$ wherein $R_6$, $R_7$, $R_9$ and t are as defined below; X is a hydrogen atom or a lower alkyl radical; Y is (i) a radical of the formula:

(ii) a radical —$CH_2OR_{12}$, (iii) a radical —$COR_{13}$, or (iv) a radical —$(CH_2)_n$—$COR_{14}$ wherein $R_{10}$, $R_{11}$, $R_{12}$, $R_{13}$, $R_{14}$ and n are as defined below; $R_2$ and $R_3$, which may be identical or different, are each a hydrogen atom, a linear or branched alkyl radical having from 1 to 20 carbon atoms, a radical —$O_6$ or a radical —$SR_6$, wherein $R_6$ is as defined below, or $R_2$ and $R_3$ may together form, with the carbon atoms from which they depend, a 5-or 6-membered ring optionally substituted by methyl groups and/or optionally interrupted by an oxygen or sulfur atom; $R_4$ is a hydrogen atom, a halogen atom, a lower alkyl radical or a radical —$OR_6$ wherein $R_6$ is as defined below; $R_5$ has the definition of $R_4$, or wherein $R_4$ and $R_5$ may be identical or different; $R_6$ is a hydrogen atom, a linear or branched alkyl radical having from 1 to 20 carbon atoms or a radical —CO—$R_9$ wherein $R_9$ is as defined below and further wherein the radicals $R_6$ may be identical or different; $R_7$ is (a) a hydrogen atom, (b) a lower alkyl radical, (c) a radical of the formula:

wherein R' and R" are as defined below, or (d) a radical —$OR_8$ wherein $R_8$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid or peptide residue; the radicals $R_9$, which may be identical or different, are each a lower alkyl radical; $R_{10}$ is a hydrogen atom or a lower alkyl radical; $R_{11}$ is a hydrogen atom, a lower alkyl radical, a radical —CO—$R_9$ or a radical —COOR$_9$; $R_{12}$ is a radical $R_6$ or a radical —$CH_2$—O—$CH_2$—$CH_2$—O—$CH_3$; $R_{13}$ is a hydrogen atom or a lower alkyl radical; $R_{14}$ is a radical —$OR_8$, or a radical of the formula:

wherein R' and R", which may be identical or different, are each a hydrogen atom, a lower alkyl radical, a mono- or polyhydroxyalkyl radical, an optionally substituted aryl radical or an amino acid or peptide or sugar residue, or R' and R" may together form, with the nitrogen atom from which they depend, a heterocycle; t is an integer equal to 0, 1 or 2; n is an integer equal to 0 or 1; or the radicals X and Y may together form a double bond-containing single radical of the formula =N—$OR_6$ or =CH—$COR_{14}$; or pharmaceutically/cosmetically acceptable salt or optical or geometric isomer thereof, and wherein at least one of $R_2$, $R_3$, and $R_4$ are not hydrogen.

2. A polyaromatic amide as defined by claim 1, wherein formula (I), Z is the radical —CO—NH—.

3. A polyaromatic amide as defined by claim 1, wherein formula (I), Z is the radical —NH—CO—.

4. A polyaromatic amide as defined by claim 1, wherein formula (I), Ar has the structure (b).

5. A polyaromatic amide as defined by claim 1, wherein formula (I), Ar has the structure (e).

6. A polyaromatic amide as defined by claim 1, which is a pharmaceutically acceptable salt thereof.

7. A polyaromatic amide as defined by claim 1, wherein formula (I), X is a hydrogen atom, Y is an —$NH_2$ group, and $R_7$ is a radical —$OR_8$.

8. A polyaromatic amide as defined by claim 1, wherein formula (I), the lower alkyl radical substituents are selected from the group consisting of methyl, ethyl, isopropyl, butyl, tert-butyl and hexyl radicals.

9. A polyaromatic amide as defined by claim 1, wherein formula (I), the linear or branched alkyl radical substituents having from 1 to 20 carbon atoms are selected from the group consisting of methyl, ethyl, propyl, 2-ethylhexyl, octyl, dodecyl, hexadecyl and octadecyl radicals.

10. A polyaromatic amide as defined by claim 1, wherein formula (I), the monohydroxyalkyl radical substituents are selected from the group consisting of 2-hydroxypropyl and 3-hydroxypropyl radicals.

11. A polyaromatic amide as defined by claim 1, wherein formula (I), the polyhydroxyalkyl radical substituents are selected from the group consisting of 2,3-dihydroxypropyl, 2,3,4-trihydroxybutyl, 2,3,4,5-tetrahydroxypentyl and pentaerythritol radicals.

12. A polyaromatic amide as defined by claim 1, wherein formula (I), the aryl radical substituents are selected from the group consisting of phenyl radicals optionally substituted by at least one halogen atom, or a hydroxyl or nitro functional group.

13. A polyaromatic amide as defined by claim 1, wherein formula (I), the aralkyl radical substituents are selected from the group consisting of benzyl and phenethyl radicals optionally substituted by at least one halogen atom, or a hydroxyl or nitro functional group.

14. A polyaromatic amide as defined by claim 1, wherein formula (I), the alkenyl radical substituents have from 1 to 5 carbon atoms and have at least one site of ethylenic unsaturation.

15. A polyaromatic amide as defined by claim 1, wherein formula (I), the sugar residue substituents are selected from the group consisting of those of glucose, galactose, mannose and glucuronic acid.

16. A polyaromatic amide as defined by claim 1, wherein formula (I), the amino acid residue substituents are selected from the group consisting of those of lysine, glycine and aspartic acid.

17. A polyaromatic amide as defined by claim 1, wherein formula (I), the peptide residue substituents are those of a dipeptide or tripeptide.

18. A polyaromatic amide as defined by claim 1, wherein formula (I), the heterocyclic radical substituents are selected from the group consisting of piperidino, morpholino, pyrrolidino and piperazino radicals which are optionally substituted by a $C_1$–$C_6$ alkyl radical or a mono- or polyhydroxyalkyl radical.

19. A polyaromatic amide as defined by claim 1, wherein formula (I), the halogen atom substituents are selected from the group consisting of fluorine, chlorine and bromine atoms.

20. A polyaromatic amide as defined by claim 1, selected from the group consisting of methyl N-methy-5-[α-amino-(5,6,7,8-tetrahydro-5,5,8,8-tetramethyl-2-naphthyl) acetamido]-2-pyrrolecarboxylate; methyl N-methy-4-[α-amino-(5,6,7,8-tetrahydro-5,5,8,8-tetramethyl-2-naphthyl) acetamido]-2-pyrrolecarboxylate; methyl N-propyl-4-[α-amino-(5,6,7,8-tetrahydro-5,5,8,8-tetramethyl-2-naphthyl) acetamido]-2-pyrrolecarboxylate.

21. A pharmaceutical composition of matter, comprising a therapeutically effective amount of a polyaromatic amide as defined by claim 1, or pharmaceutically acceptable salt or isomer thereof, and a pharmaceutically acceptable carrier or diluent therefor.

22. The pharmaceutical composition as defined by claim 21, further comprising a retinoid compound, a D vitamin or derivative thereof, a corticosteroid, an anti-free radical agent, an α-hydroxy or α-keto acid or derivative thereof, an ion channel blocker, or combination thereof.

23. The pharmaceutical composition as defined by claim 21, comprising a tablet, a capsule, a syrup, a suspension, an elixir, a solution, a powder, granules, an emulsion, microspheres, nanospheres, lipid vesicles, polymeric vesicles, or an injectable.

24. The pharmaceutical composition as defined by claim 21, comprising an ointment, a cream, a milk, a pommade, an impregnated pad, a gel, a spray, or a lotion.

25. The pharmaceutical composition as defined by claim 21, adopted for topical administration.

26. The pharmaceutical composition as defined by claim 21, adopted for systemic administration.

27. The pharmaceutical composition as defined by claim 21, comprising from 0.001% to 5% by weight of said polyaromatic amide, or salt or isomer thereof.

28. A method for treating a keratinization disorder in a mammalian organism in need of such treatment, comprising administering to such organism a therapeutically effective amount of the pharmaceutical composition as defined by claim 21.

29. A method for treating a dermalotogical disorder in a mammalian organism in need of such treatment, comprising administering to such organism a therapeutically effective amount of the pharmaceutical composition as defined by claim 21.

30. A method for treating an ophthalmological disorder in a mammalian organism in need of such treatment, comprising administering to such organism a therapeutically effective amount of the pharmaceutical composition as defined by claim 21.

31. A method for treating skin aging in a mammalian organism in need of such treatment, comprising administering to such organism a therapeutically effective amount of the pharmaceutical composition as defined by claim 21.

32. A method for treating epidermal and/or dermal atrophy in a mammalian organism in need of such treatment, comprising administering to such organism a therapeutically effective amount of the pharmaceutical composition as defined by claim 21.

33. A method for treating a cicatrization disorder in a mammalian organism in need of such treatment, comprising administering to such organism a therapeutically effective amount of the pharmaceutical composition as defined by claim 21.

34. A method for treating a sebaceous function disorder in a mammalian organism in need of such treatment, comprising administering to such organism a therapeutically effective amount of the pharmaceutical composition as defined by claim 21.

35. A method for treating a cancerous or precancerous disease state in a mammalian organism in need of such treatment, comprising administering to such organism a therapeutically effective amount of the pharmaceutical composition as defined by claim 21.

36. A method for treating inflammation in a mammalian organism in need of such treatment, comprising administering to such organism a therapeutically effective amount of the pharmaceutical composition as defined by claim 21.

37. A method for treating a viral infection in a mammalian organism in need of such treatment, comprising administering to such organism a therapeutically effective amount of the pharmaceutical composition as defined by claim 21.

38. A method for treating or preventing alopecia in a mammalian organism in need of such treatment, comprising administering to such organism a therapeutically effective amount of the pharmaceutical composition as defined by claim 21.

39. A method for treating a cardiovascular disorder in a mammalian organism in need of such treatment, comprising administering to such organism a therapeutically effective amount of the pharmaceutical composition as defined by claim 21.

40. A method for treating an immune deficiency in a mammalian organism in need of such treatment, comprising administering to such organism a therapeutically effective amount of the pharmaceutical composition as defined by claim 21.

41. A method for treating a dermatological, rheumatic, respiratory, cardiovascular or ophthalmologic disorder in a mammalian organism in need of such treatment, comprising administering to such organism a therapeutically effective amount of the pharmaceutical composition as defined by claim 21.

42. The method as defined by claim 41, comprising administering to such organism a daily dose of said polyaromatic amide of about 0.01 mg/kg to 100 is mg/kg of body weight thereof.

43. A cosmetic composition of matter, comprising a cosmetically effective amount of a polyaromatic amide as defined by claim 1, or cosmetically acceptable salt or isomer thereof, and a cosmetically acceptable carrier or diluent therefor.

44. The cosmetic composition as defined by claim 43, comprising a cream, a milk, a lotion, a gel, microspheres, nanospheres, lipid vesicles, polymeric vesicles, a soap, or a shampoo.

45. The cosmetic composition as defined by claim 43, comprising from 0.001% to 3% by weight of said polyaromatic amide, or salt or isomer thereof.

46. The cosmetic composition as defined by claim 43, further comprising a retinoid compound, a D vitamin or derivative thereof, a corticosteroid, an anti-free radical agent, an α-hydroxy or α-keto acid or derivative thereof, an ion channel blocker, or combination thereof.

47. A method for treating a skin or hair disorder on a mammalian organism in need of such treatment, comprising administering to such organism a cosmetically/therapeutically effective amount of the cosmetic composition as defined by claim 43.

48. The pharmaceutical composition as defined by claim 21, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

49. The pharmaceutical composition as defined by claim 21, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

50. The cosmetic composition by claim 43, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

51. The cosmetic composition as defined by claim 43, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *